(12) United States Patent
Moore et al.

(10) Patent No.: US 8,906,815 B2
(45) Date of Patent: Dec. 9, 2014

(54) COMPOSITE NONWOVEN FIBROUS WEBS AND METHODS OF MAKING AND USING THE SAME

(75) Inventors: Eric M. Moore, Roseville, MN (US); Michael R. Berrigan, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 495 days.

(21) Appl. No.: 12/810,113

(22) PCT Filed: Dec. 15, 2008

(86) PCT No.: PCT/US2008/086759
§ 371 (c)(1),
(2), (4) Date: Jun. 22, 2010

(87) PCT Pub. No.: WO2009/085679
PCT Pub. Date: Jul. 9, 2009

(65) Prior Publication Data
US 2010/0285101 A1 Nov. 11, 2010

Related U.S. Application Data

(60) Provisional application No. 61/017,230, filed on Dec. 28, 2007.

(51) Int. Cl.
*D04H 13/00* (2006.01)
(Continued)

(52) U.S. Cl.
CPC ........... *D04H 13/007* (2013.01); *D04H 13/002* (2013.01); *D04H 1/42* (2013.01); *B32B 5/26* (2013.01); *B32B 27/02* (2013.01); *D04H 1/4382* (2013.01); *B32B 5/14* (2013.01)
USPC ............ 442/340; 442/351; 442/400; 442/401

(58) Field of Classification Search
CPC .. D04H 1/42–1/44; D04H 1/54; D04H 1/565; D04H 13/00; D04H 13/007; D10B 2505/04; D10B 2403/03; D10B 2403/0331; D10B 2403/02; D10B 2403/0211; B01D 2239/1266; B01D 2239/0604–2239/0622; B01D 39/1623; B01D 39/16; B01D 39/083; B01D 39/163
USPC ......................... 442/340–346, 381–384, 400
See application file for complete search history.

(56) References Cited

U.S. PATENT DOCUMENTS

| 1,975,504 A | 10/1934 | Formhals |
| 3,874,886 A | 4/1975 | Levecque et al. |

(Continued)

FOREIGN PATENT DOCUMENTS

| DE | 199 29 709 | 12/2000 |
| DE | 10 2004 046 669 | 3/2006 |

(Continued)

OTHER PUBLICATIONS

Spunbond definition, Textile Glossary, Celanese Acetate, copyright 2001.*

(Continued)

*Primary Examiner* — Jennifer A Steele
(74) *Attorney, Agent, or Firm* — James A. Baker

(57) ABSTRACT

The disclosure relates to composite nonwoven fibrous webs including a population of sub-micrometer fibers having a median diameter less than one micrometer (μm), and a population of microfibers having a median diameter of at least 1 μm. At least, one of the fiber populations is oriented, and each composite nonwoven fibrous web has a thickness and exhibits a Solidity of less than 10%. The disclosure also relates to methods of making composite nonwoven fibrous webs, and articles including composite nonwoven fibrous webs made according to the methods. In exemplary applications, the articles may be used as gas filtration articles, liquid filtration articles, sound absorption articles, surface cleaning articles, cellular growth support articles, drug delivery articles, personal hygiene articles, or wound dressing articles.

12 Claims, 7 Drawing Sheets

(51) Int. Cl.
*D04H 5/06* (2006.01)
*D04H 5/08* (2012.01)
*D04H 1/42* (2012.01)
*B32B 5/26* (2006.01)
*B32B 27/02* (2006.01)
*D04H 1/4382* (2012.01)
*B32B 5/14* (2006.01)

(56) References Cited

U.S. PATENT DOCUMENTS

| | | | |
|---|---|---|---|
| 4,118,531 | A | 10/1978 | Hauser |
| 4,127,706 | A | 11/1978 | Martin et al. |
| 4,363,646 | A | 12/1982 | Torobin |
| 4,536,361 | A | 8/1985 | Torobin |
| 4,666,763 | A | 5/1987 | King et al. |
| 4,729,371 | A | 3/1988 | Krueger et al. |
| 5,227,107 | A | 7/1993 | Dickenson et al. |
| 5,332,426 | A | 7/1994 | Tang et al. |
| 5,415,779 | A | 5/1995 | Markell et al. |
| 5,496,507 | A | 3/1996 | Angadjivand et al. |
| 5,605,746 | A | 2/1997 | Groeger et al. |
| 5,855,788 | A | 1/1999 | Everhart et al. |
| 5,871,836 | A | 2/1999 | Schultink et al. |
| 6,057,256 | A | 5/2000 | Krueger et al. |
| 6,114,017 | A | 9/2000 | Fabbricante et al. |
| 6,139,308 | A | 10/2000 | Berrigan et al. |
| 6,183,670 | B1 | 2/2001 | Torobin et al. |
| 6,269,513 | B1 | 8/2001 | Torobin |
| 6,315,806 | B1 | 11/2001 | Torobin et al. |
| 6,382,526 | B1 | 5/2002 | Reneker et al. |
| 6,494,974 | B2 | 12/2002 | Riddell |
| 6,550,622 | B2 | 4/2003 | Koslow |
| 6,607,624 | B2 | 8/2003 | Berrigan et al. |
| 6,743,273 | B2 | 6/2004 | Chung et al. |
| 6,800,226 | B1 | 10/2004 | Gerking |
| 6,824,372 | B2 | 11/2004 | Berrigan et al. |
| 6,861,025 | B2 | 3/2005 | Erickson et al. |
| 6,872,311 | B2 | 3/2005 | Koslow |
| 2001/0003082 | A1* | 6/2001 | kahlbaugh et al. ............ 442/340 |
| 2002/0034624 | A1 | 3/2002 | Harpell et al. |
| 2004/0035095 | A1 | 2/2004 | Healey |
| 2004/0092185 | A1 | 5/2004 | Grafe et al. |
| 2004/0097155 | A1 | 5/2004 | Olson et al. |
| 2005/0061728 | A1 | 3/2005 | Sprenger |
| 2005/0079379 | A1 | 4/2005 | Wadsworth et al. |
| 2005/0090173 | A1 | 4/2005 | Weisman |
| 2005/0266760 | A1 | 12/2005 | Chhabra et al. |
| 2005/0287891 | A1 | 12/2005 | Park |
| 2006/0096910 | A1 | 5/2006 | Brownstein et al. |
| 2006/0096911 | A1 | 5/2006 | Brey et al. |
| 2006/0137317 | A1* | 6/2006 | Bryner et al. ............ 55/528 |
| 2007/0175817 | A1 | 8/2007 | Goldman |
| 2007/0202766 | A1 | 8/2007 | Ouellette et al. |
| 2008/0026659 | A1 | 1/2008 | Brandner et al. |
| 2008/0026661 | A1* | 1/2008 | Fox et al. ............ 442/344 |
| 2008/0038976 | A1 | 2/2008 | Berrigan et al. |
| 2008/0160856 | A1* | 7/2008 | Chen et al. ............ 442/341 |

FOREIGN PATENT DOCUMENTS

| | | |
|---|---|---|
| JP | 63-267538 | 11/1988 |
| JP | 2-104765 | 4/1990 |
| JP | 2006-289209 | 10/2006 |
| WO | 93/06924 | 4/1993 |
| WO | 00/12194 | 3/2000 |
| WO | 00/29658 | 5/2000 |
| WO | 2004/046443 | 6/2004 |
| WO | 2006/089063 A2 | 8/2006 |
| WO | 2006/118902 | 11/2006 |
| WO | 2007/001990 | 1/2007 |
| WO | 2007/047263 | 4/2007 |
| WO | 2008/085545 | 7/2008 |

OTHER PUBLICATIONS

Nihon Sen'i Kikai Gakkai Hushokuhu Kenkyukai, "Hushokuhu no. Kiso to Oyo", Nihon Sen'i Kikai Gakkaishi (The Textile Machinery Society Japan), (Aug. 25, 1993), pp. 118-119.

Yaida, "Hushokuhu (Nonwovens)", Sen'i Gakkaishi, Shadanhojin Sen'i Gakkai (The Society of Fiber Science and Technology Japan), vol. 60, Issue 6, (2004), pp. 197-201.

* cited by examiner

US 8,906,815 B2

COMPOSITE NONWOVEN FIBROUS WEBS AND METHODS OF MAKING AND USING THE SAME

CROSS REFERENCE TO RELATED APPLICATION

This application claims the benefit of U.S. Provisional Patent Application No. 61/017,230, filed Dec. 28, 2007, the disclosure of which is incorporated by reference herein in its entirety.

TECHNICAL FIELD

The present disclosure relates to composite nonwoven fibrous webs and methods of making and using such webs. The disclosure further relates to low density composite nonwoven webs including blends of sub-micrometer fibers and microfibers useful in making absorbent articles.

BACKGROUND

Nonwoven webs have been used to produce absorbent articles useful, for example, as absorbent wipes for surface cleaning, as gas and liquid absorbent or filtration media, and as barrier materials for sound absorption. In some applications requiring high absorbency, it may be desirable to use a high porosity nonwoven article made up of high surface area fine sub-micrometer fibers. Fine sub-micrometer fibers, however, have a tendency to collapse or crush in handling, thereby decreasing the porosity and/or surface area available for absorption, while increasing the pressure drop of a fluid passing through the nonwoven article. For gas and liquid filtration applications in particular, it may be desirable to maintain a low pressure drop through the nonwoven article even while maintaining high absorbency.

Some current nonwoven articles use surface modifying agents to prevent fine sub-micrometer fibers from crushing. One example of this is the use of silicone oil in polypropylene sub-micrometer fibers to prevent cold welding. Using such surface modifying agents can cause complications, for example, when the nonwoven article is used as an absorbent wipe, or as a filtration medium. Some of these complications include leaching of the surface modifying agent over time, the propensity of the surface modifying agent to contaminate other surfaces or a gas or liquid medium passing through the nonwoven article, as well as the added cost of using a surface modifying agent solely to prevent crushing. While surface modifying agents may help promote crush recovery in a fine sub-micrometer fiber web, they do little to help with overall compression strength and Solidity under compressive load.

SUMMARY

There is a continued need in the art for low density nonwoven composite articles that combine high absorbency with low pressure drop characteristics and improved crush resistance.

In one aspect, the disclosure relates to a composite nonwoven fibrous web comprising a population of sub-micrometer fibers having a median diameter less than one micrometer (µm), and a population of microfibers having a median diameter of at least 1 µm. At least, one of the fiber populations is oriented, and the composite nonwoven fibrous web has a thickness and exhibits a Solidity of less than 10%.

In another aspect, the disclosure relates to a method of making a composite nonwoven fibrous web by forming a population of sub-micrometer fibers having a median fiber diameter of less than one micrometer (µm), forming a population of microfibers having a median fiber diameter of at least 1 µm; and combining the sub-micrometer and microfibers into a composite nonwoven fibrous web. At least one of the fiber populations is oriented, and the composite nonwoven fibrous web has a thickness and exhibits a Solidity of less than 10%.

In a further aspect, the disclosure relates to an article comprising a composite nonwoven fibrous web as described and made according to the above method. In exemplary embodiments, the article may be used as a gas filtration article, a liquid filtration article, a sound absorption article, a surface cleaning article, a cellular growth support article, a drug delivery article, a personal hygiene article, or a wound dressing article.

Exemplary embodiments of the composite nonwoven fibrous webs according to the present disclosure may have structural features that enable their use in a variety of applications, have exceptional absorbent properties, exhibit high porosity and permeability due to their low Solidity, and/or be manufactured in a cost-effective manner.

Various aspects and advantages of exemplary embodiments of the present invention have been summarized. The above Summary is not intended to describe each illustrated embodiment or every implementation of the present invention. The Drawings and the Detailed Description that follow more particularly exemplify certain preferred embodiments using the principles disclosed herein.

BRIEF DESCRIPTION OF THE DRAWINGS

Exemplary embodiments of the present disclosure are further described with reference to the appended figures, wherein.

DETAILED DESCRIPTION

Glossary

Figure 1A:
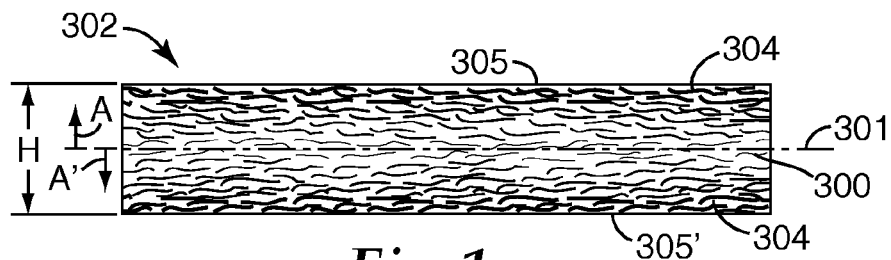
FIG. 1a is a schematic representation of an exemplary single layer composite nonwoven fibrous web according to one illustrative embodiment of the present disclosure.

As used herein:

"Microfibers" are a population of fibers having a population median diameter of at least one micrometer.

"Ultrafine microfibers" are a population of microfibers having a population median diameter of two micrometers or less.

"Sub-micrometer fibers" are a population of fibers having a population median diameter of less than one micrometer.

When reference is made herein to a batch, group, array, etc. of a particular kind of microfiber, e.g., "an array of sub-micrometer fibers," it means the complete population of microfibers in that array, or the complete population of a single batch of microfibers, and not only that portion of the array or batch that is of sub-micrometer dimensions.

"Continuous oriented microfibers" herein refers to essentially continuous fibers issuing from a die and traveling through a processing station in which the fibers are drawn and at least portions of the molecules within the fibers are oriented into alignment with the longitudinal axis of the fibers ("oriented" as used with respect to fibers means that at least portions of the molecules of the fibers are aligned along the longitudinal axis of the fibers).

"Melt-blown fibers" herein refers to fibers prepared by extruding molten fiber-forming material through orifices in a die into a high-velocity gaseous stream, where the extruded material is first attenuated and then solidifies as a mass of fibers.

"Separately prepared sub-micrometer fibers" means a stream of sub-micrometer fibers produced from a sub-micrometer fiber-forming apparatus (e.g., a die) positioned such that the sub-micrometer fiber stream is initially spatially separate (e.g., over a distance of about 1 inch (25 mm) or more from, but will merge in flight and disperse into, a stream of larger size microfibers.

"Layer" means a single stratum formed between two major surfaces. A layer may exist internally within a single web, e.g. a single stratum formed with multiple strata in a single web have first and second major surfaces defining the thickness of the web. A layer may also exist in a composite article comprising multiple webs, e.g. a single stratum in a first web having first and second major surfaces defining the thickness of the web, when that web is overlaid or underlaid by a second web having first and second major surfaces defining the thickness of the second web, in which case each of the first and second webs forms at least one layer. In addition, layers may simultaneously exist within a single web and between that web and one or more other webs, each web forming a layer.

"Adjoining" with reference to a particular first layer means joined with or attached to another, second layer, in a position wherein the first and second layers are either next to (i.e. adjacent to) and directly contacting each other, or contiguous with each other but not in direct contact (i.e. there are one or more additional layers intervening between the first and second layers).

"Autogenous bonding" is defined as bonding between fibers at an elevated temperature as obtained in an oven or with a through-air bonder without application of direct contact pressure such as in point-bonding or calendering.

"Molecularly same" polymer refers to polymers that have essentially the same repeating molecular unit, but which may differ in molecular weight, method of manufacture, commercial form, etc.

"Self supporting" or "self sustaining" in describing a web means that the web can be held, handled and processed by itself.

"Solidity" is a nonwoven web property inversely related to density and characteristic of web permeability and porosity (low Solidity corresponds to high permeability and high porosity), and is defined by the equation:

$$\text{Solidity}(\%) = \frac{[3.937 * \text{Web Basis Weight}(g/m^2)]}{[\text{Web Thickness (mils)} * \text{Bulk Density } (g/cm^3)]}$$

"Web Basis Weight" is calculated from the weight of a 10 cm×10 cm web sample.

"Web Thickness" is measured on a 10 cm×10 cm web sample using a thickness testing gauge having a tester foot with dimensions of 5 cm×12.5 cm at an applied pressure of 150 Pa.

"Bulk Density" is the bulk density of the polymer or polymer blend that makes up the web, taken from the literature.

Various exemplary embodiments of the disclosure will now be described with particular reference to the Drawings. Exemplary embodiments of the present invention may take on various modifications and alterations without departing from the spirit and scope of the disclosure. Accordingly, it is to be understood that the embodiments of the present invention are not to be limited to the following described exemplary embodiments, but is to be controlled by the limitations set forth in the claims and any equivalents thereof.

A. Composite Nonwoven Fibrous Webs

The present disclosure is directed to composite nonwoven fibrous webs that may be advantageous for absorbent articles useful, for example, as absorbent wipes for surface cleaning, as gas and liquid absorbent or filtration media, and as barrier materials for sound absorption. Exemplary embodiments of the composite nonwoven fibrous webs may have structural features that enable their use in a variety of applications, have exceptional absorbent properties, exhibit high porosity and permeability due to their low Solidity, and/or be manufactured in a cost-effective manner. Resiliency or collapse (e.g., crush) resistance is a desirable feature of exemplary preferred embodiments of the present disclosure.

Nonwoven products are routinely handled and subjected to compression stresses during both manufacture and use. Finer fibers (e.g., sub-micrometer fibers) are more likely to compress irreversibly, resulting in disadvantageous high Solidity forms exhibiting low permeability and porosity, and reduced absorbency. Certain exemplary embodiments of the present disclosure may use a multi-layer construction including an integral support layer to maintain the low Solidity of fine sub-micrometer fibers.

Various exemplary embodiments of the disclosure will now be described with particular reference to the Drawings. Exemplary embodiments of the present invention may take on various modifications and alterations without departing from the spirit and scope of the disclosure. Accordingly, it is to be understood that the embodiments of the present invention are not to be limited to the following described exemplary embodiments, but is to be controlled by the limitations set forth in the claims and any equivalents thereof.

An exemplary composite nonwoven fibrous web illustrative of the present disclosure is shown in FIG. 1a. The exemplary single-layer composite nonwoven fibrous web 302 comprises a population of sub-micrometer fibers 300 having a median diameter less than one micrometer (μm), and a population of microfibers 304 having a median diameter of at least 1 μm. At least one of the fiber populations is oriented, and the composite nonwoven fibrous web 302 has a thickness H and exhibits a Solidity of less than 10%.

In the exemplary embodiment of FIG. 1*a*, the population of sub-micrometer fibers 300 is shown more concentrated proximate the centerline 301 of the web (defined at a position of about one half of the web thickness, H from first major surface 305 and second major surface 305' of the single-layer composite nonwoven fibrous web 302), and the population of microfibers 304 is shown more concentrated proximate the first major surface 305 and second major surface 305' of the single-layer composite nonwoven fibrous web 302. In other words, the ratio of the number of sub-micrometer fibers to the number of microfibers varies across the thickness H of the composite nonwoven fibrous web 302. In the single-layer composite nonwoven fibrous web 302 illustrated in FIG. 1*a*, the ratio of the number of sub-micrometer fibers to the number of microfibers varies from a peak value proximate the centerline 301 defined by the half-thickness (i.e., H/2) of the composite nonwoven fibrous web 302, to a lower value proximate each major surface 305 and 305' of the single-layer composite nonwoven fibrous web 302. A concentration gradient from higher number concentration of sub-micrometer fibers to lower number concentration of sub-micrometer fibers thus exists in moving away from the centerline 301 in each of the directions A and A'.

Figure 1B:
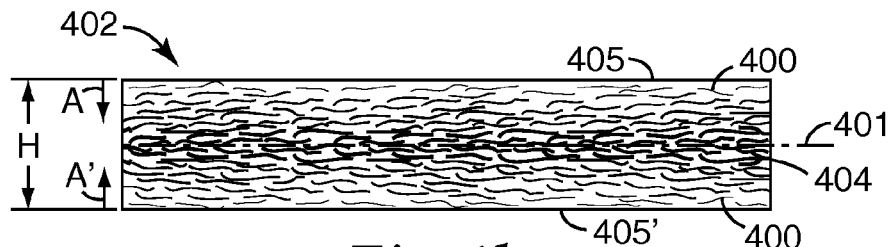
FIG. 1b is a schematic representation of another exemplary single layer composite nonwoven fibrous web according to another illustrative embodiment of the present disclosure.

Another exemplary composite nonwoven fibrous web illustrative of the present disclosure is shown in FIG. 1*b*. The exemplary single-layer composite nonwoven fibrous web 402 comprises a population of sub-micrometer fibers 400 having a median diameter less than one micrometer (μm), and a population of microfibers 404 having a median diameter of at least 1 μm. At least one of the fiber populations is oriented, and the composite nonwoven fibrous web 402 has a thickness H and exhibits a Solidity of less than 10%.

In the exemplary embodiment of FIG. 1*b*, the population of microfibers 404 is shown more concentrated proximate the centerline 401 of the web (defined at a position of about one half of the web thickness, H from first major surface 405 and second major surface 405' of the single-layer composite nonwoven fibrous web 402), and the population of sub-micrometer fibers 400 is shown more concentrated proximate the first major surface 405 and second major surface 405' of the single-layer composite nonwoven fibrous web 402. In other words, the ratio of the number of sub-micrometer fibers to the number of microfibers varies across the thickness H of the composite nonwoven fibrous web 402. In the single-layer composite nonwoven fibrous web 402 illustrated in FIG. 1*b*, the ratio of the number of sub-micrometer fibers to the number of microfibers varies from a peak value proximate each major surface 305 and 305', to a lower value proximate the centerline 401 defined by the half-thickness (i.e., H/2) of the single-layer composite nonwoven fibrous web 402. A concentration gradient from higher number concentration of sub-micrometer fibers to lower number concentration of sub-micrometer fibers thus exists in each direction A and A' until the centerline 401 is reached.

Figure 1C:
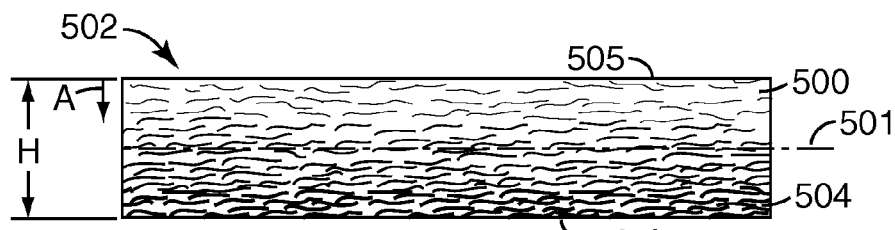
FIG. 1c is a schematic representation of an additional exemplary single layer composite nonwoven fibrous web according to an additional illustrative embodiment of the present disclosure.

An additional exemplary composite nonwoven fibrous web illustrative of the present disclosure is shown in FIG. 1*c*. The exemplary single-layer composite nonwoven fibrous web 502 comprises a population of sub-micrometer fibers 500 having a median diameter less than one micrometer (μm), and a population of microfibers 504 having a median diameter of at least 1 μm. At least one of the fiber populations is oriented, and the composite nonwoven fibrous web 502 has a thickness H and exhibits a Solidity of less than 10%.

In the exemplary embodiment of FIG. 1*c*, the population of sub-micrometer fibers 500 is shown intermixed with the population of microfibers 504 to form an inhomogenous mixture of fibers proximate the centerline 501 (defined at a position of about one half of the web thickness, H from first major surface 505 and second major surface 505') of the single-layer composite nonwoven fibrous web 502. The population of sub-micrometer fibers 500 is more concentrated proximate the first major surface 505, and the population of microfibers 504 is more concentrated proximate second major surface 505' of the single-layer composite nonwoven fibrous web 502.

The concentration of the population of sub-micrometer fibers 500 also varies such that the ratio of the number of sub-micrometer fibers to the number of microfibers decreases across the thickness of the single-layer composite nonwoven fibrous web 502 in moving from first major surface 505 to second major surface 505'. In other words, the ratio of the number of sub-micrometer fibers to the number of microfibers varies across the thickness H of the composite nonwoven fibrous web 502. In the single-layer composite nonwoven fibrous web 502 illustrated in FIG. 1*c*, the ratio of the number of sub-micrometer fibers to the number of microfibers varies from a peak value proximate major surface 505, to a lower value proximate the centerline 501 defined by the half-thickness (i.e., H/2) of the single-layer composite nonwoven fibrous web 502. A concentration gradient from higher number concentration of sub-micrometer fibers to lower number concentration of sub-micrometer fibers thus exists in direction A.

In the exemplary embodiment illustrated in FIG. 1*c*, the population of sub-micrometer fibers 500 forms an overlayer on an underlayer comprising the population of microfibers 504. In other exemplary embodiments not illustrated in the Figures, the population of microfibers 504 forms an overlayer on an underlayer comprising the population of sub-micrometer fibers 500. In further exemplary embodiments not illustrated in the Figures, the population of sub-micrometer fibers is intermixed with the population of microfibers to form a single-layer composite nonwoven fibrous web comprising an inhomogeneous mixture of fibers.

Figure 1D:
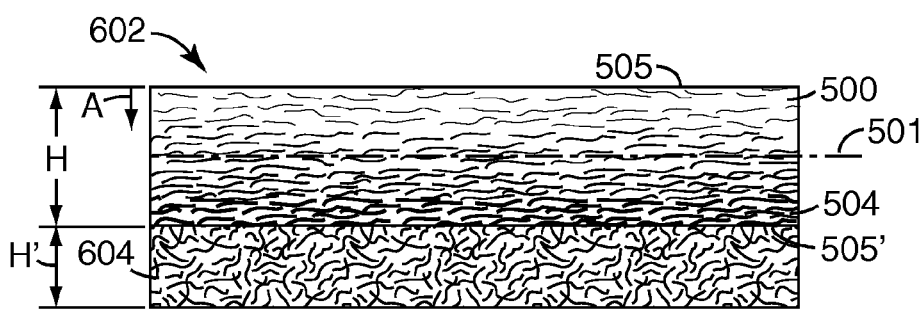
FIG. 1d is a schematic representation of an exemplary multi-layer composite nonwoven fibrous web according to one illustrative embodiment of the present disclosure.

A further exemplary composite nonwoven fibrous web illustrative of the present disclosure is shown in FIG. 1*d*. The exemplary multi-layer composite nonwoven fibrous web 602 comprises the exemplary single-layer composite nonwoven fibrous web 502 of FIG. 1*c* overlaid on a support layer 604 with second major surface 505' contacting (e.g., overlaying) the support layer. Single-layer composite nonwoven fibrous web 502 comprises a population of sub-micrometer fibers 500 having a median diameter less than one micrometer (μm), and a population of microfibers 504 having a median diameter of at least 1 μm. At least one of the fiber populations is oriented, and the composite nonwoven fibrous web 502 has a thickness H and exhibits a Solidity of less than 10%. The support layer 604 has a thickness of H', and the multi-layer composite nonwoven fibrous web 602 has a thickness of (H+H').

In the exemplary embodiment of FIG. 1*d*, the population of sub-micrometer fibers 500 is shown intermixed with the population of microfibers 504 to form an inhomogenous mixture of fibers proximate the centerline 501 (defined at a position of about one half of the web thickness, H from first major surface 505 and second major surface 505') of the single-layer composite nonwoven fibrous web 502. The population of sub-micrometer fibers 500 is more concentrated proximate the first major surface 505, and the population of microfibers 504 is more concentrated proximate second major surface 505' of the single-layer composite nonwoven fibrous web 502.

The concentration of the population of sub-micrometer fibers 500 also varies such that the ratio of the number of sub-micrometer fibers to the number of microfibers decreases across the thickness of the single-layer composite nonwoven fibrous web 502 in moving from first major surface 505 to second major surface 505'. In other words, the ratio of the number of sub-micrometer fibers to the number of microfibers varies across the thickness H of the composite nonwoven fibrous web 502. A concentration gradient from higher number concentration of sub-micrometer fibers to lower number concentration of sub-micrometer fibers thus exists in direction A.

In the multi-layer composite nonwoven fibrous web 602 illustrated in FIG. 1d, the ratio of the number of sub-micrometer fibers to the number of microfibers varies from a peak value proximate major surface 505, to a lower value proximate the centerline 501 defined by the half-thickness (i.e., H/2) of the single-layer composite nonwoven fibrous web 502. Thus, the population of sub-micrometer fibers 500 forms an overlayer on an underlayer comprising the population of microfibers 504, and second major surface 505' of single-layer composite nonwoven fibrous web 502 adjoins and overlays the support layer 604.

Figure 1E:
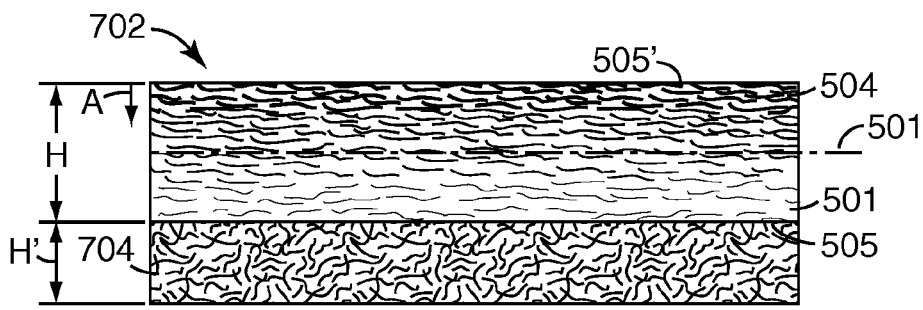
FIG. 1e is a schematic representation of another exemplary multi-layer composite nonwoven fibrous web according to another illustrative embodiment of the present disclosure.

An additional exemplary composite nonwoven fibrous web illustrative of the present disclosure is shown in FIG. 1e. The exemplary multi-layer composite nonwoven fibrous web 702 of FIG. 1e comprises the exemplary single-layer composite nonwoven fibrous web 502 of FIG. 1c positioned adjoining a support layer 704 with first major surface 505 contacting (e.g., overlaying) the support layer 704. The composite nonwoven fibrous web 502 has a thickness H and exhibits a Solidity of less than 10%. The support layer 704 has a thickness of H', and the multi-layer composite nonwoven fibrous web 702 has a thickness of (H+H').

In certain embodiments, single-layer composite nonwoven fibrous web 502 of FIG. 1c may be flipped 180 degrees about the centerline 501 before contacting the first major surface 505 with support layer 704. Alternatively, the population of sub-micrometer fibers 500 may be formed on support layer 704 and the population of microfibers 504 may be added to the population of sub-micrometer fibers 500.

In the exemplary embodiment of FIG. 1e, the population of sub-micrometer fibers 500 is shown intermixed with the population of microfibers 504 to form an inhomogenous mixture of fibers proximate the centerline 501 (defined at a position of about one half of the web thickness, H from first major surface 505 and second major surface 505') of the single-layer composite nonwoven fibrous web 502. The population of sub-micrometer fibers 500 is more concentrated proximate the first major surface 505, and the population of microfibers 504 is more concentrated proximate second major surface 505' of the single-layer composite nonwoven fibrous web 502. A concentration gradient from higher number concentration of microfibers to lower number concentration of microfibers thus exists in direction A.

In the multi-layer composite nonwoven fibrous web 702 illustrated in FIG. 1e, the ratio of the number of sub-micrometer fibers to the number of microfibers varies from a peak value proximate major surface 505, to a lower value proximate the centerline 501 defined by the half-thickness (i.e., H/2) of the single-layer composite nonwoven fibrous web 502. Thus, the population of microfibers 504 forms an overlayer on an underlayer comprising the population of sub-micrometer fibers 500, and first major surface 505 of single-layer composite nonwoven fibrous web 502 adjoins and overlays the support layer 704.

In other exemplary embodiments not illustrated in the Figures, a multi-layer composite nonwoven fibrous web is formed by overlaying on a support layer a single-layer composite nonwoven fibrous web comprising an overlayer of microfibers on an underlayer comprising a population of sub-micrometer fibers, such that at least a portion of the sub-micrometer fibers contact the support layer at a major surface of the single-layer composite nonwoven web.

In additional exemplary embodiments not illustrated in the Figures, a multi-layer composite nonwoven fibrous web is formed by overlaying on a support layer a single-layer composite web comprising a population of sub-micrometer fibers intermixed with a population of microfibers to form an inhomogenous mixture of fibers on the support layer. In further embodiments, a multi-layer composite nonwoven fibrous web is formed by overlaying on a support layer a single-layer composite web as shown in any of FIG. 1a, 1b or 1c, such that a major surface of the single-layer composite web (e.g., 305, 305', 405, 405', 505, or 505') contacts the support layer. Furthermore, a support layer may have additional layers and/or components (not shown) adjacent to or adjoining the support layer opposite the major surface of the single-layer composite web contacting the support layer.

In each of the preceding embodiments of a multi-layer composite nonwoven fibrous web, it will be understood that the term "overlayer" is intended to describe the embodiments actually illustrated by FIGS. 1d and 1e. However, by flipping any of the illustrated multi-layer composite nonwoven fibrous webs 180 degrees about the indicated centerline (e.g., 501 in FIGS. 1d and 1e), what has been described as an overlayer may become an underlayer, and the disclosure is intended to cover such modification to the illustrated embodiments. Furthermore, reference to "a layer" is intended to mean at least one layer, and therefore each illustrated embodiment of a multi-layer composite nonwoven fibrous web may include one or more additional layers (not shown) within the scope of the disclosure. Furthermore, reference to "a layer" is intended to describe a layer at least partially covering one or more additional layers (not shown).

For any of the previously described exemplary embodiments of a composite nonwoven fibrous web according to the present disclosure, the single-layer composite nonwoven fibrous web will exhibit a basis weight, which may be varied depending upon the particular end use of the web. Typically, the single-layer composite nonwoven fibrous web has a basis weight of less than about 1000 grams per square meter (gsm). In some embodiments, the single-layer composite nonwoven fibrous web has a basis weight of from about 1.0 gsm to about 500 gsm. In other embodiments, the single-layer composite nonwoven fibrous web has a basis weight of from about 10 gsm to about 300 gsm.

As with the basis weight, the single-layer composite nonwoven fibrous web will exhibit a thickness, which may be varied depending upon the particular end use of the web. Typically, the single-layer composite nonwoven fibrous web has a thickness of less than about 300 millimeters (mm). In some embodiments, the single-layer composite nonwoven fibrous web has a thickness of from about 0.5 mm to about 150 mm. In other embodiments, the single-layer composite nonwoven fibrous web has a thickness of from about 1.0 mm to about 50 mm.

Various components of exemplary composite nonwoven fibrous webs according to the present disclosure will now be described.

B. Composite Nonwoven Fibrous Web Components

In one aspect, the disclosure relates to a composite nonwoven fibrous web including a population of sub-micrometer fibers having a median diameter less than one micrometer (μm), and a population of microfibers having a median diameter of at least 1 μm. At least, one of the fiber populations is oriented, and the composite nonwoven fibrous web has a thickness and exhibits a Solidity of less than 10%.

Oriented fibers are fibers where there is molecular orientation within the fiber. Fully oriented and partially oriented polymeric fibers are known and commercially available. Orientation of fibers can be measured in a number of ways, including birefringence, heat shrinkage, X-ray scattering, and elastic modulus (see e.g., *Principles of Polymer Processing*, Zehev Tadmor and Costas Gogos, John Wiley and Sons, New York, 1979, pp. 77-84). It is important to note that molecular orientation is distinct from crystallinity, as both crystalline and amorphous materials can exhibit molecular orientation independent from crystallization. Thus, even though commercially known sub-micrometer fibers made by melt-blowing or electrospinning are not oriented, there are known methods of imparting molecular orientation to fibers made using those processes. However, the process described by Torobin (see e.g., U.S. Pat. No. 4,536,361) has not been shown to produce molecularly oriented fibers.

Furthermore, it has not heretofore been known to control Solidity to less than 10% by controlling the ratio of the number of sub-micrometer fibers to the number of microfibers within a single-layer composite nonwoven fibrous web, or to use a support layer to provide a low Solidity multi-layer composite nonwoven fibrous web.

Composite nonwoven fibrous webs of the present disclosure may comprise one or more of the following components.

1. Sub-Micrometer Fiber Component

The composite nonwoven fibrous webs of the present disclosure comprise one or more fine sub-micrometer fiber components such as sub-micrometer fiber component 300 of exemplary composite nonwoven fibrous web 302 shown in FIG. 1*a*. In some embodiments, a preferred fine sub-micrometer fiber component is a sub-micrometer fiber component comprising fibers having a median fiber diameter of less than one micrometer (μm). In some exemplary embodiments, the sub-micrometer fiber component comprises fibers have a median fiber diameter ranging from about 0.2 μm to about 0.9 μm. In other exemplary embodiments, the sub-micrometer fiber component comprises fibers have a median fiber diameter ranging from about 0.5 μm to about 0.7 μm.

In the present disclosure, the "median fiber diameter" of fibers in a given sub-micrometer fiber component is determined by producing one or more images of the fiber structure, such as by using a scanning electron microscope; measuring the fiber diameter of clearly visible fibers in the one or more images resulting in a total number of fiber diameters, x; and calculating the median fiber diameter of the x fiber diameters. Typically, x is greater than about 50, and desirably ranges from about 50 to about 200.

In some exemplary embodiments, the sub-micrometer fiber component may comprise one or more polymeric materials. Suitable polymeric materials include, but are not limited to, polyolefins such as polypropylene and polyethylene; polyesters such as polyethylene terephthalate and polybutylene terephthalate; polyamide (Nylon-6 and Nylon-6,6); polyurethanes; polybutene; polylactic acids; polyvinyl alcohol; polyphenylene sulfide; polysulfone; liquid crystalline polymers; polyethylene-co-vinylacetate; polyacrylonitrile; cyclic polyolefins; polyoxymethylene; polyolefinic thermoplastic elastomers; or a combination thereof The sub-micrometer fiber component may comprise monocomponent fibers comprising any one of the above-mentioned polymers or copolymers. In this exemplary embodiment, the monocomponent fibers may contain additives as described below, but comprise a single fiber-forming material selected from the above-described polymeric materials. Further, in this exemplary embodiment, the monocomponent fibers typically comprise at least 75 weight percent of any one of the above-described polymeric materials with up to 25 weight percent of one or more additives. Desirably, the monocomponent fibers comprise at least 80 weight percent, more desirably at least 85 weight percent, at least 90 weight percent, at least 95 weight percent, and as much as 100 weight percent of any one of the above-described polymeric materials, wherein all weights are based on a total weight of the fiber.

The sub-micrometer fiber component may also comprise multi-component fibers formed from (1) two or more of the above-described polymeric materials and (2) one or more additives as described below. As used herein, the term "multi-component fiber" is used to refer to a fiber formed from two or more polymeric materials. Suitable multi-component fiber configurations include, but are not limited to, a sheath-core configuration, a side-by-side configuration, and an "islands-in-the-sea" (for example, fibers produced by Kuraray Company, Ltd., Okayama, Japan) configuration.

For sub-micrometer fiber components formed from multi-component fibers, desirably the multi-component fiber comprises (1) from about 75 to about 99 weight percent of two or more of the above-described polymers and (2) from about 25 to about 1 weight percent of one or more additional fiber-forming materials based on the total weight of the fiber.

2. Microfiber Component

The composite nonwoven fibrous webs of the present disclosure comprise one or more coarse fiber components such as microfiber component 304 of exemplary composite nonwoven fibrous web 302 shown in FIG. 1*a*. In some embodiments, a preferred coarse fiber component is a microfiber component comprising fibers having a median fiber diameter of at least 1 μm. In some exemplary embodiments, the microfiber component comprises fibers have a median fiber diameter ranging from about 2 μm to about 100 μm. In other exemplary embodiments, the microfiber component comprises fibers have a median fiber diameter ranging from about 5 μm to about 50 μm.

In the present disclosure, the "median fiber diameter" of fibers in a given microfiber component is determined by producing one or more images of the fiber structure, such as by using a scanning electron microscope; measuring the fiber diameter of clearly visible fibers in the one or more images resulting in a total number of fiber diameters, x; and calculating the median fiber diameter of the x fiber diameters. Typically, x is greater than about 50, and desirably ranges from about 50 to about 200.

In some exemplary embodiments, the microfiber component may comprise one or more polymeric materials. Generally, any fiber-forming polymeric material may be used in preparing the microfiber, though usually and preferably the fiber-forming material is semi-crystalline. The polymers commonly used in fiber formation, such as polyethylene, polypropylene, polyethylene terephthalate, nylon, and urethanes, are especially useful. Webs have also been prepared from amorphous polymers such as polystyrene. The specific polymers listed here are examples only, and a wide variety of other polymeric or fiber-forming materials are useful.

Suitable polymeric materials include, but are not limited to, polyolefins such as polypropylene and polyethylene; polyesters such as polyethylene terephthalate and polybutylene terephthalate; polyamide (Nylon-6 and Nylon-6,6); polyurethanes; polybutene; polylactic acids; polyvinyl alcohol; polyphenylene sulfide; polysulfone; liquid crystalline polymers; polyethylene-co-vinylacetate; polyacrylonitrile; cyclic polyolefins; polyoxymethylene; polyolefinic thermoplastic elastomers; or a combination thereof.

A variety of natural fiber-forming materials may also be made into nonwoven microfibers according to exemplary embodiments of the present disclosure. Preferred natural materials may include bitumen or pitch (e.g., for making carbon fibers). The fiber-forming material can be in molten form or carried in a suitable solvent. Reactive monomers can also be employed, and reacted with one another as they pass to or through the die. The nonwoven webs may contain a mixture of fibers in a single layer (made for example, using two closely spaced die cavities sharing a common die tip), a plurality of layers (made for example, using a plurality of die cavities arranged in a stack), or one or more layers of multi-component fibers (such as those described in U.S. Pat. No. 6,057,256 (Krueger et al.).

Fibers also may be formed from blends of materials, including materials into which certain additives have been blended, such as pigments or dyes. Bi-component microfibers, such as core-sheath or side-by-side bi-component fibers, may be prepared ("bi-component" herein includes fibers with two or more components, each component occupying a part of the cross-sectional area of the fiber and extending over a substantial length of the fiber), as may be bicomponent sub-micrometer fibers. However, exemplary embodiments of the disclosure may be particularly useful and advantageous with monocomponent fibers (in which the fibers have essentially the same composition across their cross-section, but "monocomponent" includes blends or additive-containing materials, in which a continuous phase of substantially uniform composition extends across the cross-section and over the length of the fiber). Among other benefits, the ability to use single-component fibers reduces complexity of manufacturing and places fewer limitations on use of the web.

In addition to the fiber-forming materials mentioned above, various additives may be added to the fiber melt and extruded to incorporate the additive into the fiber. Typically, the amount of additives is less than about 25 wt %, desirably, up to about 5.0 wt %, based on a total weight of the fiber. Suitable additives include, but are not limited to, particulates, fillers, stabilizers, plasticizers, tackifiers, flow control agents, cure rate retarders, adhesion promoters (for example, silanes and titanates), adjuvants, impact modifiers, expandable microspheres, thermally conductive particles, electrically conductive particles, silica, glass, clay, talc, pigments, colorants, glass beads or bubbles, antioxidants, optical brighteners, antimicrobial agents, surfactants, fire retardants, and fluorochemicals.

One or more of the above-described additives may be used to reduce the weight and/or cost of the resulting fiber and layer, adjust viscosity, or modify the thermal properties of the fiber or confer a range of physical properties derived from the physical property activity of the additive including electrical, optical, density-related, liquid barrier or adhesive tack related properties.

3. Optional Support Layer

The composite nonwoven fibrous webs of the present disclosure may further comprise a support layer such as support layer 604 of exemplary multi-layer composite nonwoven fibrous article 602 shown in FIG. 1*d*. When present, the support layer may provide most of the strength of the composite nonwoven fibrous article. In some embodiments, the above-described sub-micrometer fiber component tends to have very low strength, and can be damaged during normal handling. Attachment of the sub-micrometer fiber component to a support layer lends strength to the sub-micrometer fiber component, while retaining the low Solidity and hence the desired absorbent properties of the sub-micrometer fiber component. A multi-layer composite nonwoven fibrous web structure may also provide sufficient strength for further processing, which may include, but is not limited to, winding the web into roll form, removing the web from a roll, molding, pleating, folding, stapling, weaving, and the like.

A variety of support layers may be used in the present disclosure. Suitable support layers include, but are not limited to, a nonwoven fabric, a woven fabric, a knitted fabric, a foam layer, a film, a paper layer, an adhesive-backed layer, a foil, a mesh, an elastic fabric (i.e., any of the above-described woven, knitted or nonwoven fabrics having elastic properties), an apertured web, an adhesive-backed layer, or any combination thereof. In one exemplary embodiment, the support layer comprises a polymeric nonwoven fabric. Suitable nonwoven polymeric fabrics include, but are not limited to, a spunbonded fabric, a meltblown fabric, a carded web of staple length fibers (i.e., fibers having a fiber length of less than about 100 mm), a needle-punched fabric, a split film web, a hydroentangled web, an airlaid staple fiber web, or a combination thereof. In certain exemplary embodiments, the support layer comprises a web of bonded staple fibers. As described further below, bonding may be effected using, for example, thermal bonding, adhesive bonding, powdered binder bonding, hydroentangling, needlepunching, calendering, or a combination thereof.

The support layer may have a basis weight and thickness depending upon the particular end use of the composite nonwoven fibrous article. In some embodiments of the present disclosure, it is desirable for the overall basis weight and/or thickness of the composite nonwoven fibrous article to be kept at a minimum level. In other embodiments, an overall minimum basis weight and/or thickness may be required for a given application. Typically, the support layer has a basis weight of less than about 150 grams per square meter (gsm). In some embodiments, the support layer has a basis weight of from about 5.0 gsm to about 100 gsm. In other embodiments, the support layer has a basis weight of from about 10 gsm to about 75 gsm.

As with the basis weight, the support layer may have a thickness, which varies depending upon the particular end use of the composite nonwoven fibrous article. Typically, the support layer has a thickness of less than about 150 millimeters (mm). In some embodiments, the support layer has a thickness of from about 1.0 mm to about 35 mm. In other embodiments, the support layer has a thickness of from about 2.0 mm to about 25 mm.

In certain exemplary embodiments, the support layer may comprise a microfiber component, for example, a plurality of microfibers. In such embodiments, it may be preferred to deposit the above-described sub-micrometer fiber population directly onto the microfiber support layer to form a multi-layer composite nonwoven fibrous web. Optionally, the above-described microfiber population may be deposited with or over the sub-micrometer fiber population on the microfiber support layer. In certain exemplary embodiments, the plurality of microfibers comprising the support layer are compositionally the same as the population of microfibers forming the overlayer.

The sub-micrometer fiber component may be permanently or temporarily bonded to a given support layer. In some embodiments of the present disclosure, the sub-micrometer fiber component is permanently bonded to the support layer (i.e., the sub-micrometer fiber component is attached to the support layer with the intention of being permanently bonded thereto).

In some embodiments of the present disclosure, the above-described sub-micrometer fiber component may be temporarily bonded to (i.e., removable from) a support layer, such as a release liner. In such embodiments, the sub-micrometer fiber component may be supported for a desired length of time on a temporary support layer, and optionally further processed on a temporary support layer, and subsequently permanently bonded to a second support layer.

In one exemplary embodiment of the present disclosure, the support layer comprises a spunbonded fabric comprising polypropylene fibers. In a further exemplary embodiment of the present disclosure, the support layer comprises a carded web of staple length fibers, wherein the staple length fibers comprise: (i) low-melting point or binder fibers; and (ii) high-melting point or structural fibers. Typically, the binder fibers have a melting point of at least 10° C. less than a melting point of the structural fibers, although the difference between the melting point of the binder fibers and structural fibers may be greater than 10° C. Suitable binder fibers include, but are not limited to, any of the above-mentioned polymeric fibers. Suitable structural fibers include, but are not limited to, any of the above-mentioned polymeric fibers, as well as inorganic fibers such as ceramic fibers, glass fibers, and metal fibers; and organic fibers such as cellulosic fibers.

In certain presently preferred embodiments, the support layer comprises a carded web of staple length fibers, wherein the staple length fibers comprise a blend of PET monocomponent, and PET/coPET bicomponent staple fibers. In one exemplary presently preferred embodiment, the support layer comprises a carded web of staple length fibers, wherein the staple length fibers comprise: (i) about 20 wt % bicomponent binder fibers (Invista T254 fibers commercially available from Invista, Inc. (Wichita, Kans.)) (12 d×1.5"); and (ii) about 80 wt % structural fibers (Invista T293 PET fibers (32 d×3").

As described above, the support layer may comprise one or more layers in combination with one another. In one exemplary embodiment, the support layer comprises a first layer, such as a nonwoven fabric or a film, and an adhesive layer on the first layer opposite the sub-micrometer fiber component. In this embodiment, the adhesive layer may cover a portion of or the entire outer surface of the first layer. The adhesive may comprise any known adhesive including pressure-sensitive adhesives, heat activatable adhesives, etc. When the adhesive layer comprises a pressure-sensitive adhesive, the composite nonwoven fibrous article may further comprise a release liner to provide temporary protection of the pressure-sensitive adhesive.

4. Optional Additional Layers

The composite nonwoven fibrous webs of the present disclosure may comprise additional layers in combination with the sub-micrometer fiber component, the support layer, or both. One or more additional layers may be present over or under an outer surface of the sub-micrometer fiber component (for example, over first major surface 505 of single-layer composite nonwoven fibrous web 502 of FIG. 1d), under an outer surface of the support layer (for example, under support layer 604 opposite second major surface 505' of FIG. 1d), or both.

Suitable additional layers include, but are not limited to, a color-containing layer (e.g., a print layer); any of the above-described support layers; one or more additional sub-micrometer fiber components having a distinct average fiber diameter and/or physical composition; one or more secondary fine sub-micrometer fiber layers for additional insulation performance (such as a melt-blown web or a fiberglass fabric); foams; layers of particles; foil layers; films; decorative fabric layers; membranes (i.e., films with controlled permeability, such as dialysis membranes, reverse osmosis membranes, etc.); netting; mesh; wiring and tubing networks (i.e., layers of wires for conveying electricity or groups of tubes/pipes for conveying various fluids, such as wiring networks for heating blankets, and tubing networks for coolant flow through cooling blankets); or a combination thereof.

5. Optional Attachment Devices

In certain exemplary embodiments, the composite nonwoven fibrous webs of the present disclosure may further comprise one or more attachment devices to enable the composite nonwoven fibrous article to be attached to a substrate. As discussed above, an adhesive may be used to attach the composite nonwoven fibrous article. In addition to adhesives, other attachment devices may be used. Suitable attachment devices include, but are not limited to, any mechanical fastener such as screws, nails, clips, staples, stitching, thread, hook and loop materials, etc.

The one or more attachment devices may be used to attach the composite nonwoven fibrous article to a variety of substrates. Exemplary substrates include, but are not limited to, a vehicle component; an interior of a vehicle (i.e., the passenger compartment, the motor compartment, the trunk, etc.); a wall of a building (i.e., interior wall surface or exterior wall surface); a ceiling of a building (i.e., interior ceiling surface or exterior ceiling surface); a building material for forming a wall or ceiling of a building (e.g., a ceiling tile, wood component, gypsum board, etc.); a room partition; a metal sheet; a glass substrate; a door; a window; a machinery component; an appliance component (i.e., interior appliance surface or exterior appliance surface); a surface of a pipe or hose; a computer or electronic component; a sound recording or reproduction device; a housing or case for an appliance, computer, etc.

C. Methods of Making Composite Nonwoven Fibrous Webs

The present disclosure is also directed to methods of making the composite nonwoven fibrous webs. In another aspect, the disclosure relates to a method of making a composite nonwoven fibrous web by forming a population of sub-micrometer fibers having a median fiber diameter of less than one micrometer (μm), forming a population of microfibers having a median fiber diameter of at least 1 μm; and combining the sub-micrometer and microfibers into a composite nonwoven fibrous web. At least one of the fiber populations is oriented, and the composite nonwoven fibrous web has a thickness and exhibits a Solidity of less than 10%.

Processes that are capable of producing oriented fibers include: oriented film filament formation, melt-spinning, plexifilament formation, spunbonding, wet spinning, and dry spinning. Suitable processes for producing oriented fibers are also known in the art (see, for example, Ziabicki, Andrzej, *Fundamentals of Fibre Formation: The Science of Fibre Spinning and Drawing*, Wiley, London, 1976.). Orientation does not need to be imparted within a fiber during initial fiber formation, and may be imparted after fiber formation, most commonly using drawing or stretching processes.

In some exemplary embodiments, a composite nonwoven fibrous web may be formed of sub-micrometer fibers commingled with coarser microfibers providing a support structure for the sub-micrometer nonwoven fibers. The support structure may provide the resiliency and strength to hold the fine sub-micrometer fibers in the preferred low Solidity form. The support structure could be made from a number of different components, either singly or in concert. Examples of supporting components include, for example, microfibers, discontinuous oriented fibers, natural fibers, foamed porous cellular materials, and continuous or discontinuous non oriented fibers.

In one exemplary embodiment, a microfiber stream is formed and a sub-micrometer fiber stream is separately formed and added to the microfiber stream to form the composite nonwoven fibrous web. In another exemplary embodiment, a sub-micrometer fiber stream is formed and a microfiber stream is separately formed and added to the sub-micrometer fiber stream to form the composite nonwoven fibrous web. In these exemplary embodiments, either one or both of the sub-micrometer fiber stream and the microfiber stream is oriented. In an additional embodiment, an oriented sub-micrometer fiber stream is formed and discontinuous microfibers are added to the sub-micrometer fiber stream, e.g. using a process as described in U.S. Pat. No. 4,118,531 (Hauser).

In some exemplary embodiments, the method of making a composite nonwoven fibrous web comprises combining the sub-micrometer fiber population and the microfiber population into a composite nonwoven fibrous web by mixing fiber streams, hydroentangling, wet forming, plexifilament formation, or a combination thereof. In combining the sub-micrometer fiber population with the microfiber population, multiple streams of one or both types of fibers may be used, and the streams may be combined in any order. In this manner, nonwoven composite fibrous webs may be formed exhibiting various desired concentration gradients and/or layered structures.

For example, in certain exemplary embodiments, the population of sub-micrometer fibers may be combined with the population of microfibers to form an inhomogenous mixture of fibers. In other exemplary embodiments, the population of sub-micrometer fibers may be formed as an overlayer on an underlayer comprising the population of microfibers. In certain other exemplary embodiments, the population of microfibers may be formed as an overlayer on an underlayer comprising the population of sub-micrometer fibers.

In other exemplary embodiments, the composite nonwoven fibrous article may be formed by depositing the population of sub-micrometer fibers onto a support layer, the support layer optionally comprising microfibers, so as to form a population of sub-micrometer fibers on the support layer or substrate. The method may comprise a step wherein the support layer, which optionally comprises polymeric microfibers, is passed through a fiber stream of sub-micrometer fibers having a median fiber diameter of less than 1 micrometer (μm). While passing through the fiber stream, sub-micrometer fibers may be deposited onto the support layer so as to be temporarily or permanently bonded to the support layer. When the fibers are deposited onto the support layer, the fibers may optionally bond to one another, and may further harden while on the support layer.

In certain presently preferred embodiments, the sub-micrometer fiber population is combined with an optional support layer that comprises at least a portion of the microfiber population. In other presently preferred embodiments, the sub-micrometer fiber population is combined with an optional support layer and subsequently combined with at least a portion of the microfiber population.

1. Formation of Sub-Micrometer Fibers

A number of processes may be used to produce and deposit the sub-micrometer fibers, including, but not limited to melt blowing, melt spinning, electrospinning, gas jet fibrillation, or combination thereof. Particularly suitable processes include, but are not limited to, processes disclosed in U.S. Pat. No. 3,874,886 (Levecque et al.), U.S. Pat. No. 4,363,646 (Torobin), U.S. Pat. No. 4,536,361 (Torobin), U.S. Pat. No. 5,227,107 (Dickenson et al.), U.S. Pat. No. 6,183,670 (Torobin), U.S. Pat. No. 6,743,273 (Chung et al.), U.S. Pat. No. 6,800,226 (Gerking), and DE 19929709 C2 (Gerking).

Suitable processes for forming sub-micrometer fibers also include electrospinning processes, for example, those processes described in U.S. Pat. No. 1,975,504 (Formhals). Other suitable processes for forming sub-micrometer fibers are described in U.S. Pat. No. 6,114,017 (Fabbricante et al.), U.S. Pat. No. 6,382,526 B1 (Reneker et al.), and U.S. Pat. No. 6,861,025 B2 (Erickson et al.).

Figure 2:
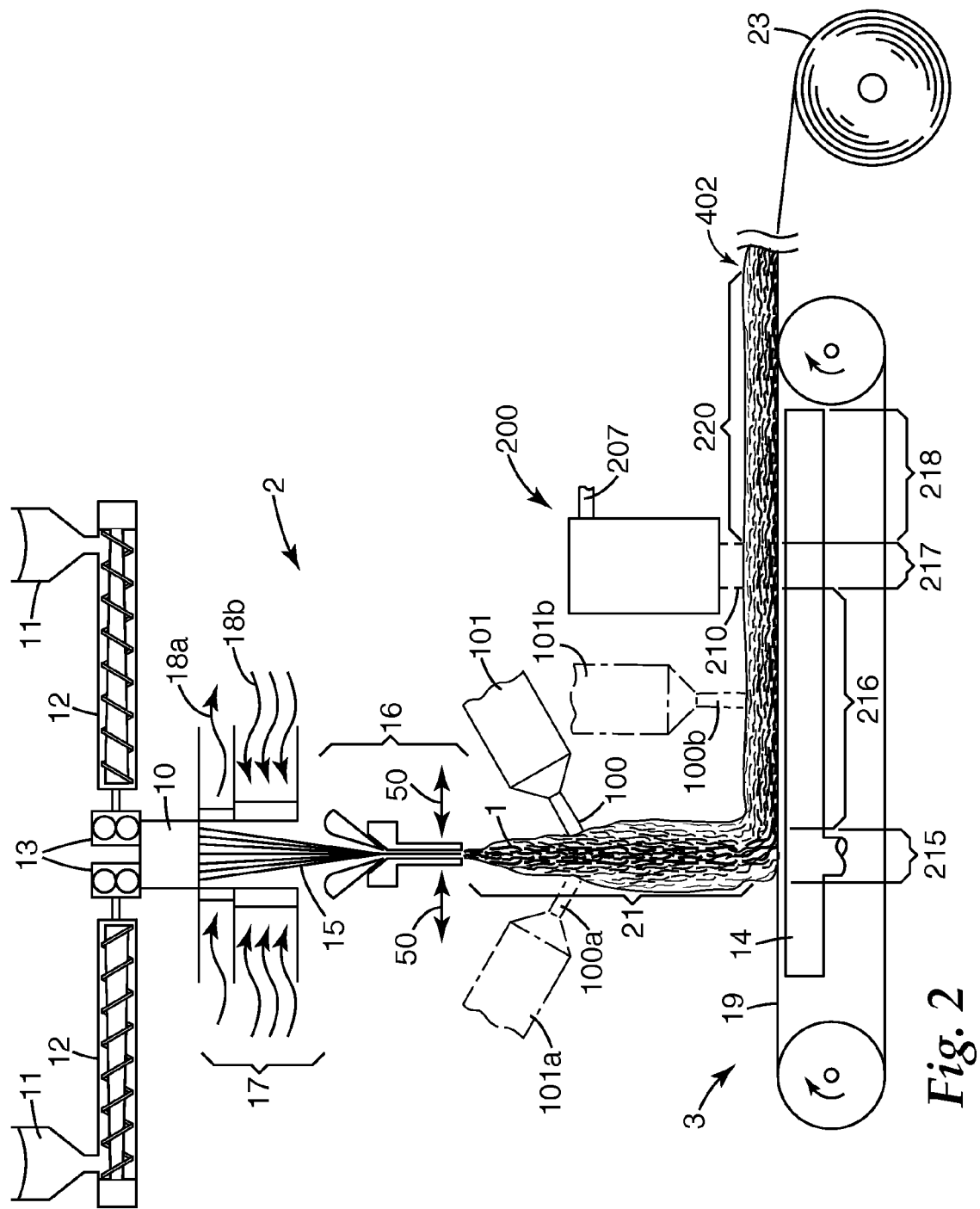
FIG. 2 is a schematic overall diagram of an exemplary apparatus for forming a composite nonwoven fibrous web according to certain illustrative embodiments of the present disclosure.

The methods of making composite nonwoven fibrous webs of the present disclosure may be used to form a sub-micrometer fiber component containing fibers formed from any of the above-mentioned polymeric materials. Typically, the sub-micrometer fiber forming method step involves melt extruding a thermoformable material at a melt extrusion temperature ranging from about 130° C. to about 350° C. A die assembly and/or coaxial nozzle assembly (see, for example, the Torobin process referenced above) comprises a population of spinnerets and/or coaxial nozzles through which molten thermoformable material is extruded. In one exemplary embodiment, the coaxial nozzle assembly comprises a population of coaxial nozzles formed into an array so as to extrude multiple streams of fibers onto a support layer or substrate. See, for example, U.S. Pat. No. 4,536,361 (FIG. 2) and U.S. Pat. No. 6,183,670 (FIGS. 1-2).

2. Formation of Microfibers

A number of processes may be used to produce and deposit the population of microfibers, including, but not limited to, melt blowing, melt spinning, filament extrusion, plexifilament formation, spunbonding, wet spinning, dry spinning, or a combination thereof. Suitable processes for forming microfibers are described in U.S. Pat. No. 6,315,806 (Torobin), U.S. Pat. No. 6,114,017 (Fabbricante et al.), U.S. Pat. No. 6,382,526 B1 (Reneker et al.), and U.S. Pat. No. 6,861,025 B2 (Erickson et al.). Alternatively, a population of microfibers may be formed or converted to staple fibers and combined with a population of sub-micrometer fibers using, for example, using a process as described in U.S. Pat. No. 4,118,531 (Hauser). In certain exemplary embodiments, the population of microfibers comprises a web of bonded microfibers, wherein bonding is achieved using thermal bonding, adhesive bonding, powdered binder, hydroentangling, needlepunching, calendering, or a combination thereof, as described below.

3. Apparatus for Forming Composite Nonwoven Fibrous Webs

Figure 3:
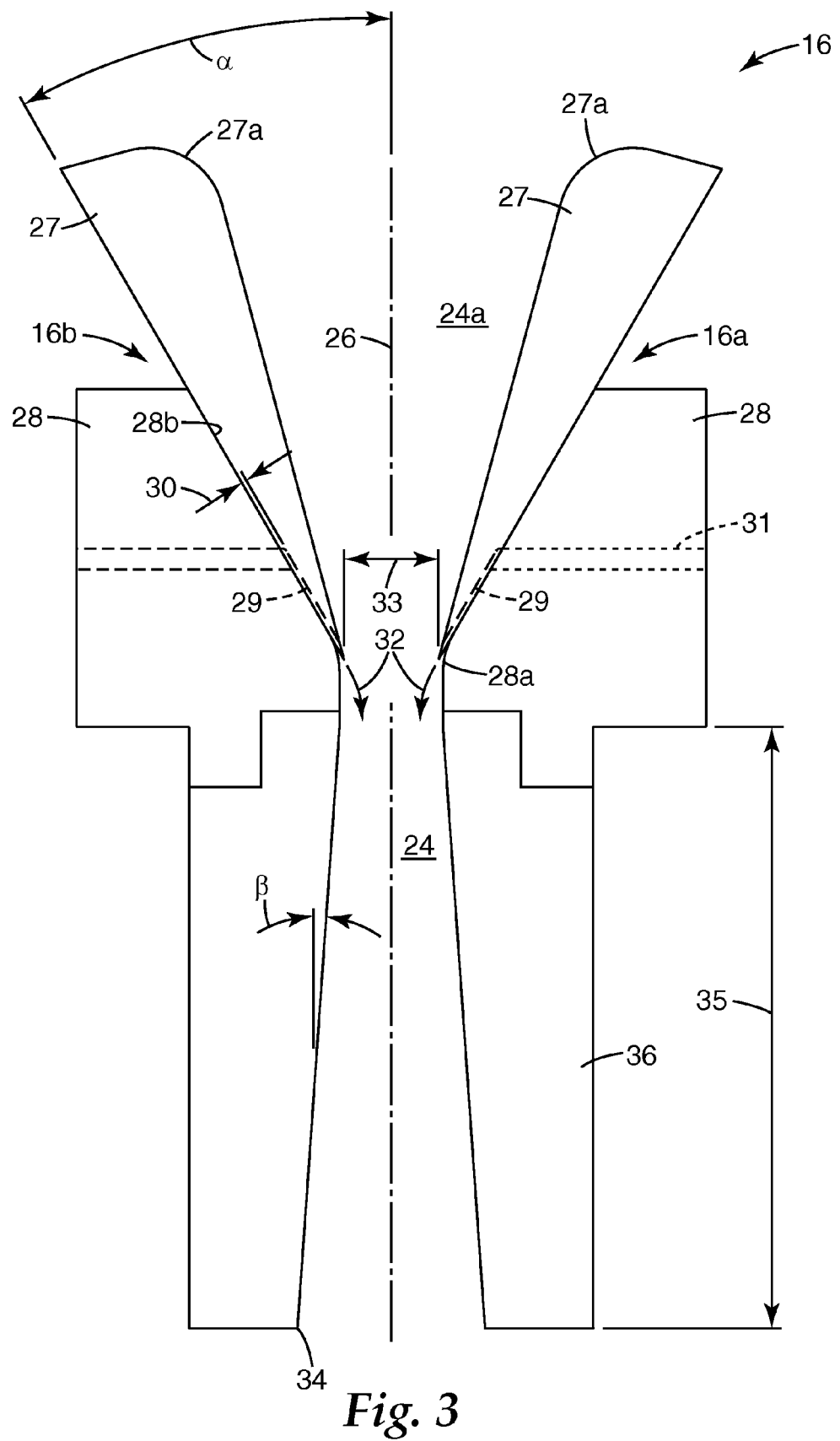
FIG. 3 is an enlarged side view of an exemplary processing chamber for preparing fibers useful in forming a composite nonwoven fibrous web according to certain illustrative embodiments of the present disclosure, with mounting means for the chamber not shown.
Figure 4:
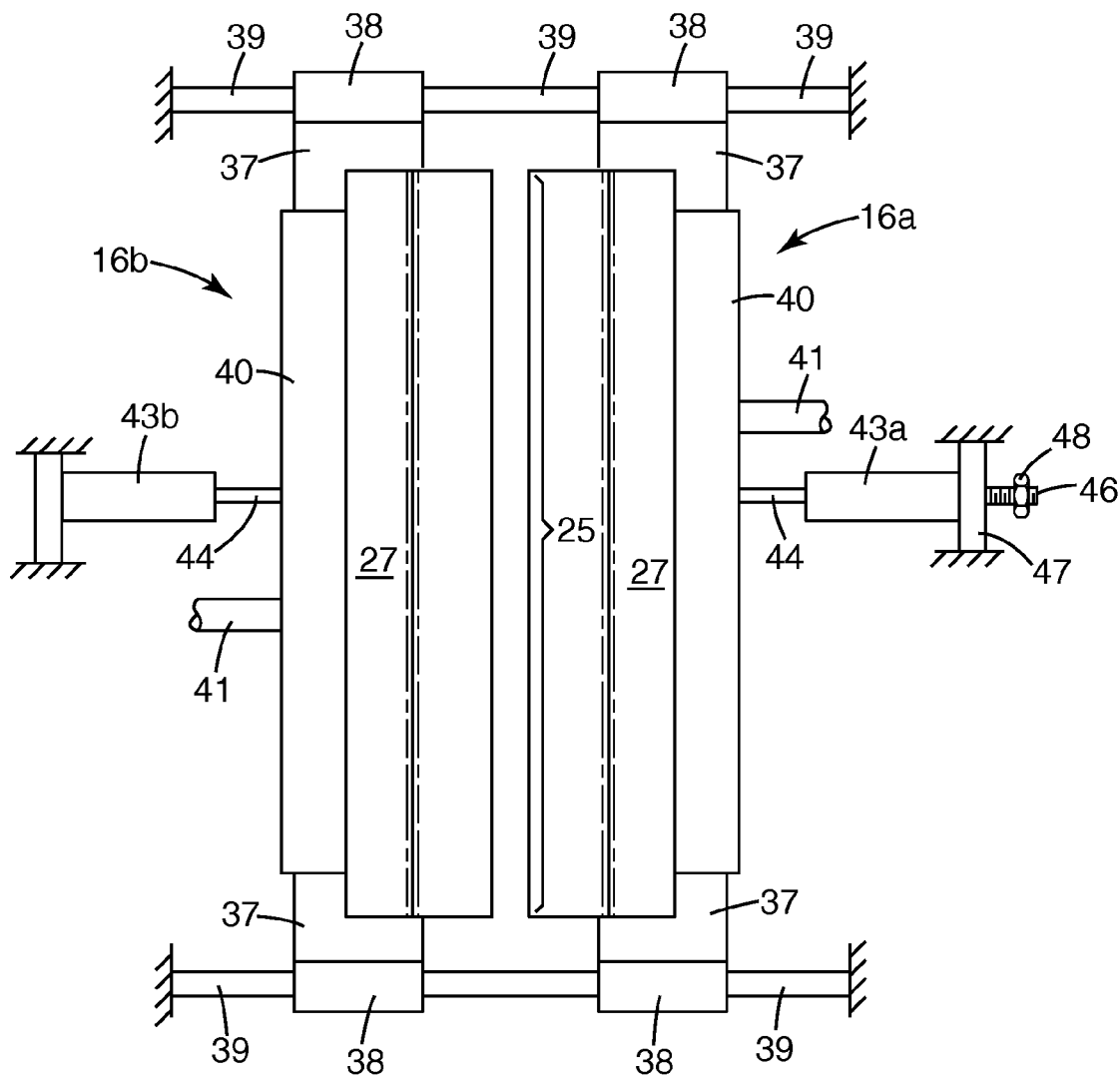
FIG. 4 is a top view, partially schematic, of the exemplary processing chamber shown in FIG. 3 together with mounting and other associated apparatus.
Figure 5:
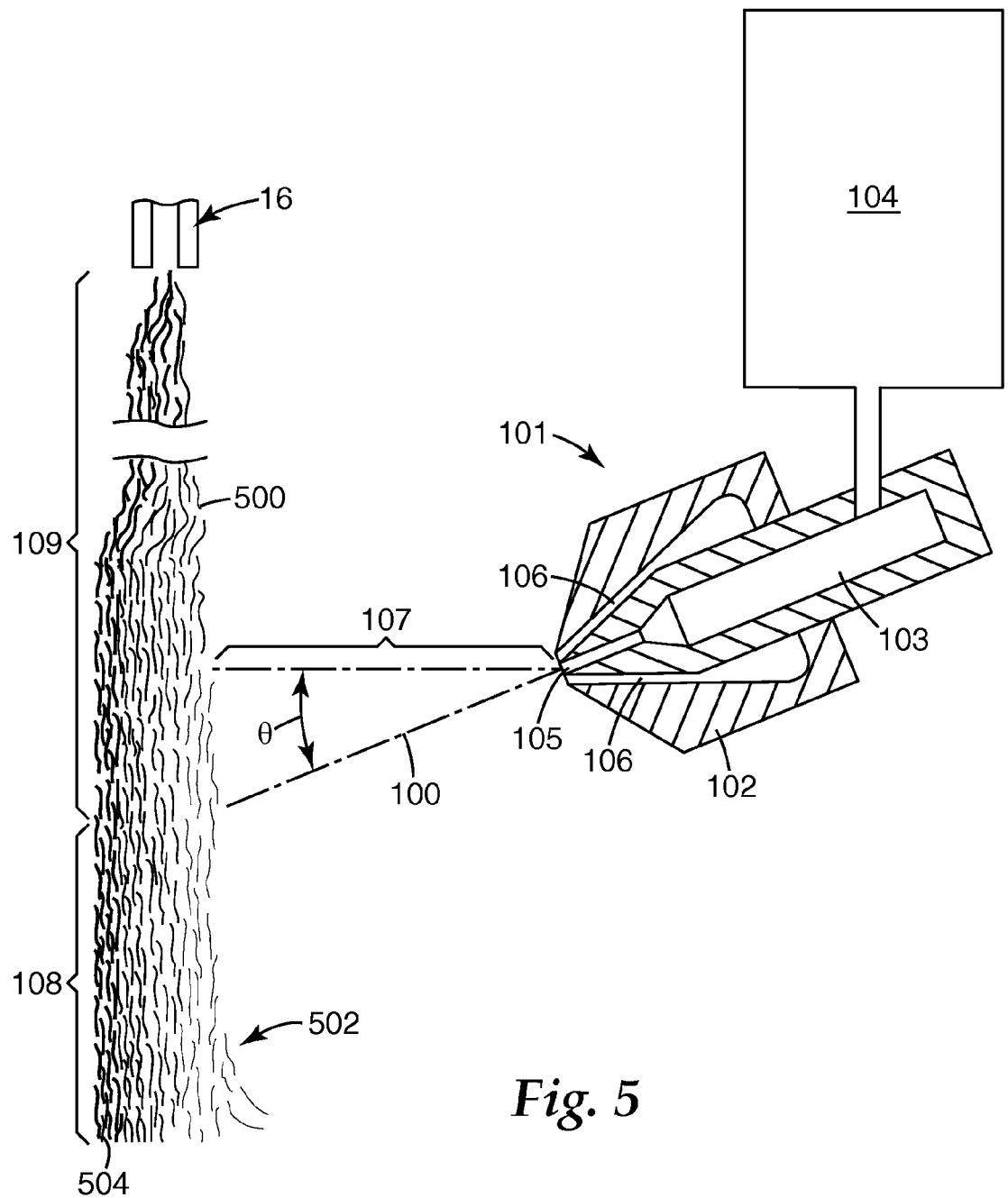
FIG. 5 is an enlarged view of a portion of the exemplary apparatus shown in FIG. 2, showing a fiber-forming die.
Figure 6:
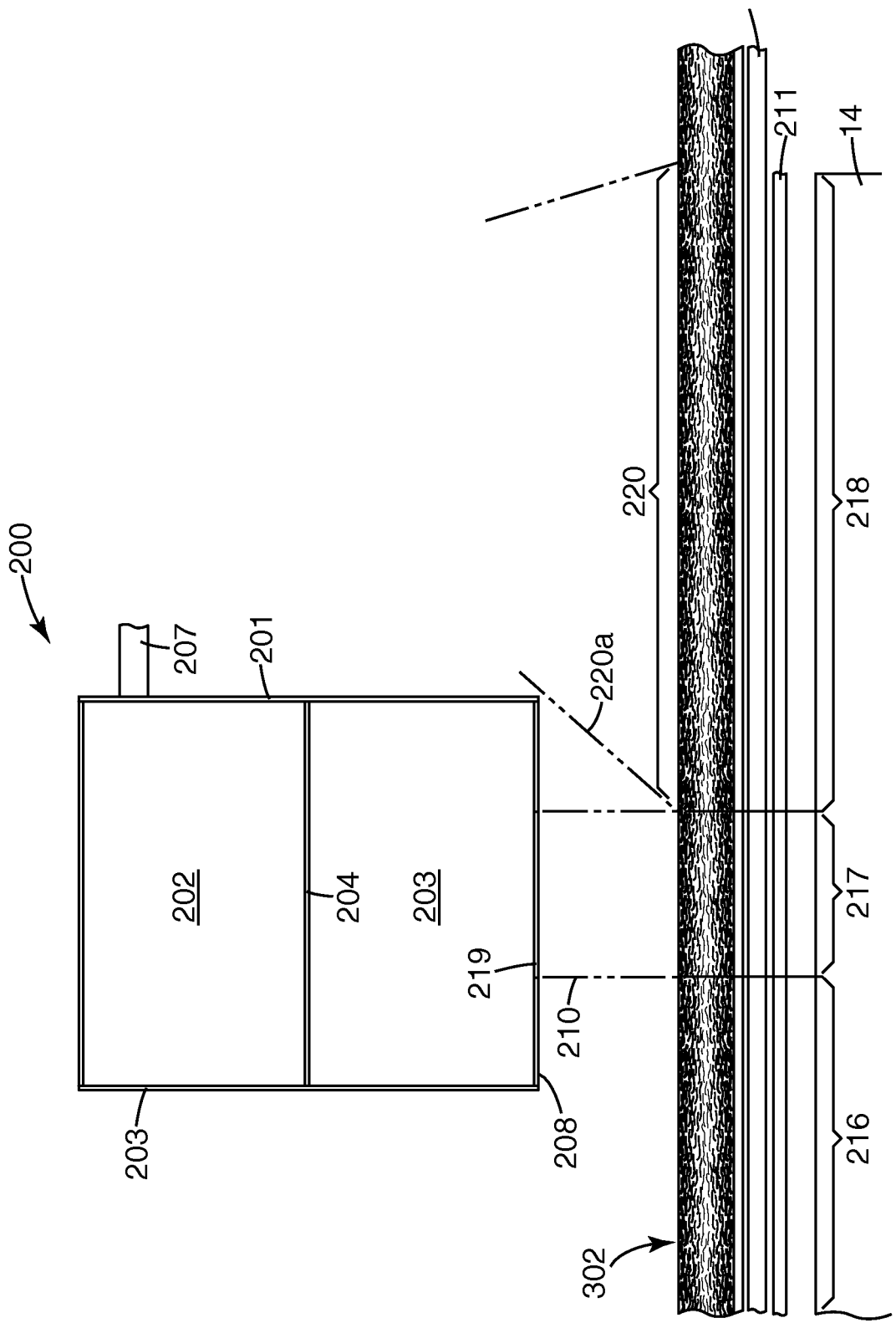
FIG. 6 is a schematic enlarged and expanded view of the optional heat-treating part of the exemplary apparatus shown in FIG. 2.
Figure 7:
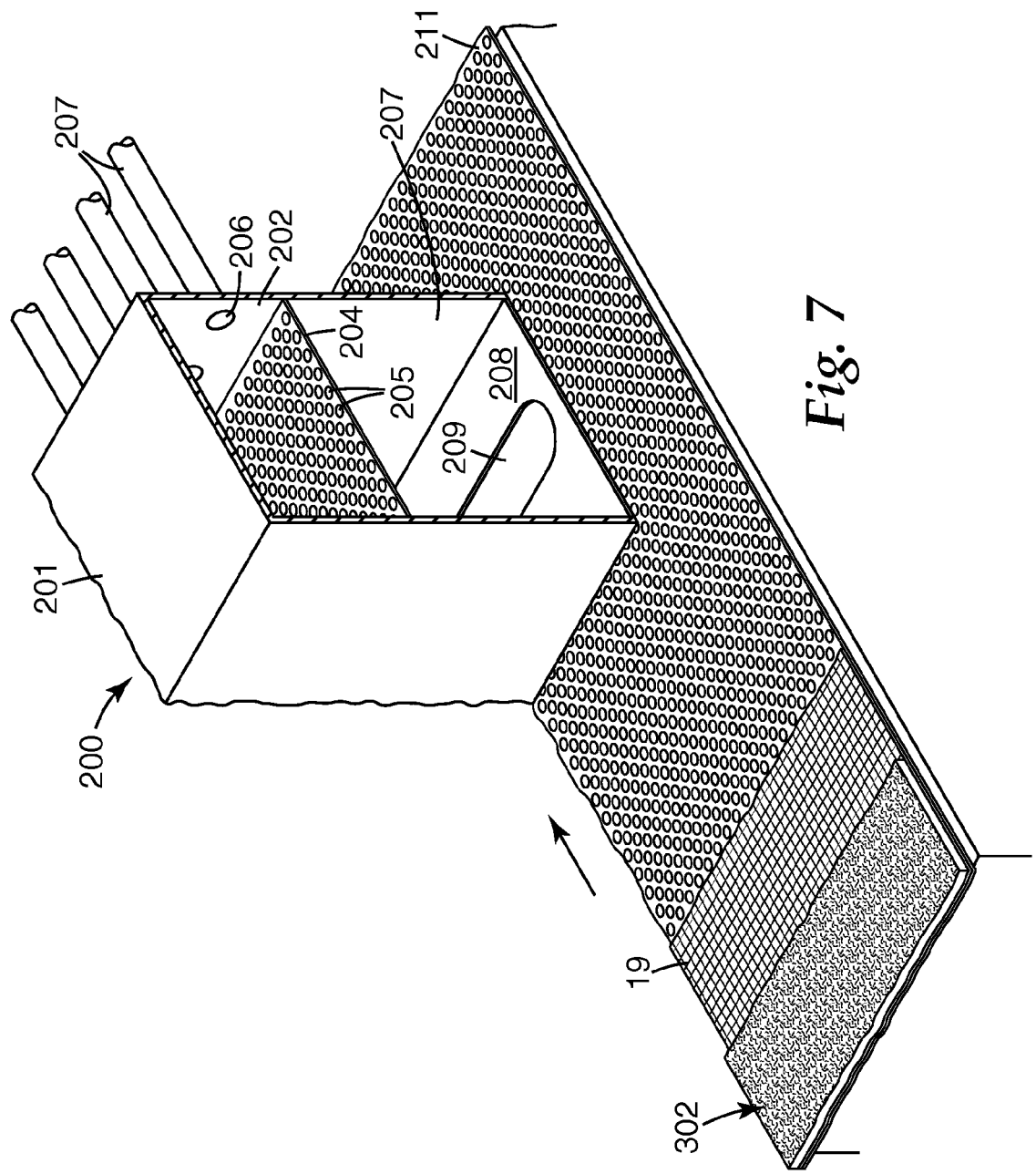
FIG. 7 is a perspective view of the apparatus of FIG. 6.

FIGS. 2-6 show an illustrative apparatus for carrying out various embodiments of the disclosure as part of an exemplary apparatus for forming a composite nonwoven fibrous web. FIG. 2 is a schematic overall side view; FIGS. 2 and 3 are enlarged views of fiber-forming portions of the FIG. 2 apparatus; FIGS. 4 and 5 are enlarged views of other portions of the apparatus shown in FIG. 2; and FIG. 7 is a perspective view of apparatus as shown in FIGS. 1 and 5.

As generally illustrated in FIG. 2, a stream 1 of continuous microfibers is prepared in microfiber-forming apparatus 2 and directed toward collection apparatus 3. On its course between the microfiber-forming apparatus 2 and the collection apparatus 3, the stream 1 is intercepted by a stream 100 of sub-micrometer fibers emanating from sub-micrometer fiber-forming apparatus 101. As shown in phantom lines in FIG. 2, an optional second stream 100a of sub-micrometer fibers may be introduced into the stream of microfibers from sub-micrometer fiber-forming die 101a. The streams merge as discussed in more detail below and become deposited on the collection apparatus 3 as a blended composite nonwoven fibrous web 402 (as illustrated in FIG. 1b) of the population of microfibers and the population of sub-micrometer fibers, such that at least one of the fiber populations is oriented, and the composite nonwoven fibrous web 402 has a thickness and exhibits a Solidity of less than 10%.

As shown in FIG. 2, an optional third stream 100b of sub-micrometer fibers may be introduced into the stream of microfibers while the composite nonwoven fibrous web 402 is transported on a continuous screen-type collector 19 past optional sub-micrometer fiber-forming die 101b. Optionally, sub-micrometer fiber-forming die 101b may be used to form the sub-micrometer fibers either alone or in combination with one or both of optional sub-micrometer fiber-forming die 101a and/or sub-micrometer fiber-forming die 101.

Exemplary embodiments of the present invention may be practiced by collecting the composite nonwoven fibrous web on a continuous screen-type collector such as the belt-type collector 19 as shown in FIG. 2, on a screen-covered drum (not shown), or using alternative methods known in the art. In one exemplary alternative collection method, a web can be collected by aiming the merged stream of microfibers and sub-micrometer fibers into the gap between two collectors, as shown and described in Olson et al., WO 2004/046443, whereupon a web having a C-shaped configuration of fibers may be obtained.

The microfiber-forming apparatus 2 in FIG. 2 is one exemplary apparatus for use in practicing certain embodiments of the present disclosure. In using this apparatus, fiber-forming material is brought to an extrusion head 10 in this illustrative apparatus, by introducing a polymeric fiber-forming material into a hopper 11, melting the material in an extruder 12, and pumping the molten material into the extrusion head 10 through a pump 13. Although solid polymeric material in pellet or other particulate form is most commonly used and melted to a liquid, pumpable state, other fiber-forming liquids such as polymer solutions can also be used.

The extrusion head 10 may be a conventional spinnerette or spin pack, generally including multiple orifices arranged in a regular pattern, e.g., straight-line rows. Filaments 15 of fiber-forming liquid are extruded from the extrusion head and conveyed to a processing chamber or optional attenuator 16. The distance 17 the extruded filaments 15 travel before reaching the optional attenuator 16 can vary, as can the conditions to which they are exposed. Typically, quenching streams 18 of air or other gas are presented to the extruded filaments to reduce the temperature of the extruded filaments 15. Alternatively, the streams of air or other gas may be heated to facilitate drawing of the fibers.

In some exemplary embodiments, there may be one or more streams of air or other fluid, for example, a first air stream 18a blown transversely to the filament stream, which may remove undesired gaseous materials or fumes released during extrusion; and a second quenching air stream 18b that achieves a major desired temperature reduction. Additional quenching streams may be used; for example, the stream shown as 18b in FIG. 2 could itself comprise more than one stream to achieve a desired level of quenching. Depending on the process being used or the form of finished product desired, the quenching air may be sufficient to solidify the extruded filaments 15 before they reach the optional attenuator 16. In other cases the extruded filaments are still in a softened or molten condition when they enter the optional attenuator. Alternatively, no quenching streams are used; in such a case ambient air or other fluid between the extrusion head 10 and the optional attenuator 16 may be a medium for any change in the extruded filaments before they enter the optional attenuator.

The filaments 15 pass through the optional attenuator 16, and eventually exit onto a collector 19 where they are collected as a mass of fibers 20, as discussed in more detail below. The collector 19 is generally porous and a gas-withdrawal device 14 can be positioned below the collector to assist deposition of fibers onto the collector. The distance 21 between the optional attenuator exit and the collector may be varied to obtain different effects.

In the optional attenuator the filaments are lengthened and reduced in diameter and polymer molecules in the filaments become oriented, i.e., at least portions of the polymer molecules within the fibers become aligned with the longitudinal axis of the fibers. In the case of semi-crystalline polymers, the orientation is generally sufficient to develop strain-induced crystallinity, which greatly strengthens the resulting fibers. FIG. 3 is an enlarged side view of a representative optional attenuator 16 for preparing microfibers that are especially useful in webs of the present disclosure. The optional attenuator 16 comprises two movable halves or sides 16a and 16b separated so as to define between them the processing chamber 24: the facing surfaces of the sides 16a and 16b form the walls of the chamber. FIG. 4 is a top and somewhat schematic view at a different scale showing the representative optional attenuator 16 and some of its mounting and support structure. As seen from the top view in FIG. 4, the processing or attenuation chamber 24 is generally an elongated slot, having a transverse length 25 (transverse to the path of travel of filaments through the optional attenuator).

Although existing as two halves or sides, the optional attenuator functions as one unitary device and will be first discussed in its combined form. (The structure shown in FIGS. 2 and 3 is representative only, and a variety of different constructions may be used.) The representative optional attenuator 16 includes slanted entry walls 27, which define an entrance space or throat 24a of the attenuation chamber 24. The entry walls 27 preferably are curved at the entry edge or surface 27a to smooth the entry of air streams carrying the extruded filaments 15. The walls 27 are attached to a main body portion 28, and may be provided with a recessed area 29 to establish a gap 30 between the body portion 28 and wall 27. Air may be introduced into the gaps 30 through conduits 31, creating air knives (represented by the arrows 32) that increase the velocity of the filaments traveling through the optional attenuator, and that also have a further quenching effect on the filaments. The optional attenuator body 28 is preferably curved at 28a to smooth the passage of air from the air knife 32 into the passage 24. The angle ($\alpha$) of the surface 28b of the optional attenuator body can be selected to determine the desired angle at which the air knife impacts a stream of filaments passing through the optional attenuator. Instead of being near the entry to the chamber, the air knives may be disposed further within the chamber.

FIG. 3 illustrates an exemplary attenuation chamber that may be useful in practicing embodiments of the present disclosure. The optional attenuator 16 may comprise an attenuation chamber 24 that may have a uniform gap width (the horizontal distance 33 on the page of FIG. 3 between the two optional attenuator sides is herein called the gap width) over its longitudinal length through the optional attenuator (the dimension along a longitudinal axis 26 through the attenuation chamber is called the axial length). Alternatively, as illustrated in FIG. 3, the gap width may vary along the length of the optional attenuator chamber. In a different embodiment, the attenuation chamber is defined by straight or flat walls; in such embodiments the spacing between the walls may be constant over their length, or alternatively the walls may slightly diverge or converge (preferred because it tends to cause a widening of the microfiber stream) over the axial length of the attenuation chamber. In all these cases, the walls defining the attenuation chamber are regarded as parallel herein, because the deviation from exact parallelism is relatively slight. As illustrated in FIG. 3, the walls defining the main portion of the longitudinal length of the passage 24 may take the form of plates 36 that are separate from, and attached to, the main body portion 28.

The length of the attenuation chamber 24 can be varied to achieve different effects; variation is especially useful with the portion between the air knives 32 and the exit opening 34, sometimes called herein the chute length 35. The angle between the chamber walls and the axis 26 may be wider near the exit 34 to change the distribution of fibers onto the collector; or structure such as deflector surfaces, curved surfaces exhibiting the Coanda effect, and uneven wall lengths may be used at the exit to achieve a desired spreading or other distribution of fibers. In general, the gap width, chute length, attenuation chamber shape, etc. are chosen in conjunction with the material being processed and the mode of treatment desired to achieve desired effects. For example, longer chute lengths may be useful to increase the crystallinity of prepared fibers. Conditions are chosen and can be widely varied to process the extruded filaments into a desired fiber form.

As illustrated in FIG. 4, the two sides 16a and 16b of the representative optional attenuator 16 are each supported through mounting blocks 37 attached to linear bearings 38 that slide on rods 39. The bearing 38 has a low-friction travel on the rod through means such as axially extending rows of ball-bearings disposed radially around the rod, whereby the sides 16a and 16b can readily move toward and away from one another. The mounting blocks 37 are attached to the optional attenuator body 28 and a housing 40 through which air from a supply pipe 41 is distributed to the conduits 31 and air knives 32.

In this illustrative embodiment, air cylinders 43a and 43b are connected, respectively, to the optional attenuator sides 16a and 16b through connecting rods 44 and apply a clamping force pressing the optional attenuator sides 16a and 16b toward one another. Some useful modes of operation of the optional attenuator 16 are described in U.S. Pat. No. 6,607,624 (Berrigan et al.). For example, movement of the optional attenuator sides or chamber walls may occur when there is a perturbation of the system, such as when a filament being processed breaks or tangles with another filament or fiber.

As will be seen, in the optional attenuator 16 illustrated in FIGS. 2 and 3, there are no side walls at the ends of the transverse length of the chamber. The result is that fibers passing through the chamber can spread outwardly outside the chamber as they approach the exit of the chamber. Such a spreading can be desirable to widen the mass of fibers collected on the collector. In other embodiments, the processing chamber does include side walls, though a single side wall at one transverse end of the chamber is not attached to both chamber sides 16a and 16b, because attachment to both chamber sides would prevent separation of the sides as discussed above. Instead, a sidewall(s) may be attached to one chamber side and move with that side when and if it moves in response to changes of pressure within the passage. In other embodiments, the side walls are divided, with one portion attached to one chamber side, and the other portion attached to the other chamber side, with the sidewall portions preferably overlapping if it is desired to confine the stream of processed fibers within the processing chamber.

Although the apparatus shown in FIGS. 2-3 with movable walls has advantages as described, use of such an optional attenuator is not necessary to practice all embodiments of the present invention. Fibers useful in certain exemplary embodiments of the present invention may be prepared on apparatus in which the walls of the optional attenuator are fixed and unmovable, or do not move in practice.

Various processes conventionally used as adjuncts to fiber-forming processes may be used in connection with filaments as they enter or exit from the optional attenuator, such as spraying of finishes or other materials onto the filaments, application of an electrostatic charge to the filaments, application of water mists, etc. In addition, various materials may be added to a collected web, including bonding agents, adhesives, finishes, and other webs or films.

Referring now to FIG. 5, in one illustrative embodiment, an exemplary apparatus for forming a composite nonwoven fibrous web 502 as shown in FIG. 1c is provided. The exemplary apparatus includes optional attenuator 16 which produces microfiber stream 500; and sub-micrometer fiber-forming apparatus 101. The sub-micrometer fiber-forming apparatus 101 can be of known structure and operated in known ways to produce sub-micrometer fibers for use in exemplary embodiments of the present invention.

For example, sub-micrometer fiber-forming apparatus 101 may include sub-micrometer fiber-forming die 102 which has an extrusion chamber 103 through which liquefied sub-micrometer fiber-forming material is advanced from an extruder 104; die orifices 105 arranged in line across the forward end of the die and through which the sub-micrometer fiber-forming material is extruded; and cooperating gas orifices 106 through which a gas, typically heated air, is forced at very high velocity. The high-velocity gaseous stream draws out and attenuates the extruded sub-micrometer fiber-forming material, whereupon the sub-micrometer fiber-forming material solidifies (to varying degrees of Solidity) and forms a stream of sub-micrometer fibers 100 comprising a population of sub-micrometer fibers 502 during travel to its point of merger with the stream of microfibers 500 comprising a population of microfibers 504.

In certain illustrated embodiments, the sub-micrometer fiber-forming die 102 is preferably positioned near the stream 500 comprising the population of microfibers 504 to best achieve capture the stream 100 comprising the population of sub-micrometer fibers 502 by the microfibers; close placement of the meltblowing die to the microfiber stream may be especially important for capture of sub-micrometer-size fibers. For example, the distance 107 in FIG. 5, from the exit of the die 102 to the centerline of the microfiber stream 1 is preferably about 2 to 12 inches (5 to 25 centimeters) and preferably about 6 or 8 inches (about 15 or 20 centimeters) or less for very small microfibers. Also, the stream 100 of sub-micrometer fibers is preferably disposed at an acute angle θ to the stream 1 of microfibers, so that a vector of the sub-micrometer fiber stream 100 is directionally aligned with the stream 1. Preferably, θ is between about 0 and 45 degrees and more preferably between 10 and 30 degrees.

The distance 108 from the approximate point of joinder of the sub-micrometer fiber stream 100 and the microfiber stream 500 to the collector 19 is typically at least 10 but less than 40 centimeters to avoid over-entangling and to retain web uniformity. The distance 109 is sufficient, generally at least 6 inches (about 15 centimeters), for the momentum of the microfiber stream to be reduced and thereby allow the sub-micrometer fiber stream to better merge with the microfiber stream.

Sub-micrometer fibers are typically very long, though they are generally regarded as discontinuous. Their long lengths—with a length-to-diameter ratio approaching infinity in contrast to the finite lengths of staple fibers—causes them to be better held within the matrix of microfibers. They are usually organic and polymeric and often of the molecularly same polymer as the microfibers. As the streams of sub-micrometer fiber and microfibers merge, the sub-micrometer fibers become dispersed among the microfibers. A rather uniform mixture may be obtained, especially in the x-y dimensions, with the distribution in the z dimension being controlled by particular process steps such as control of the distance 107, the angle θ, and the mass and velocity of the merging streams. The merged stream continues to the collector 19 in FIG. 2 and there is collected as a web-like composite nonwoven fibrous web 302.

The relative amount of sub-micrometer fibers to microfibers included in a nonwoven composite fibrous web of the present disclosure can be varied depending on the intended use of the web. An effective amount, i.e., an amount effective to accomplish desired performance, need not be large in weight amount. Usually the microfibers account for at least one weight percent and less than about 75 weight percent of the fibers of the web. Because of the high surface area of the microfibers, a small weight amount may accomplish desired performance. In the case of webs that include very small microfibers, the microfibers generally account for at least 5 percent of the fibrous surface area of the web, and more typically 10 or 20 percent or more of the fibrous surface area. A particular advantage of exemplary embodiments of the present invention is the ability to present small-diameter fibers to a needed application such as filtration or thermal or acoustic insulation.

Depending on the condition of the microfibers and sub-micrometer fibers, some bonding may occur between the fibers during collection. However, further bonding between the microfibers in the collected web is usually needed to provide a matrix of desired coherency, making the web more handle able and better able to hold the sub-micrometer fibers within the matrix ("bonding" fibers means adhering the fibers together firmly, so they generally do not separate when the web is subjected to normal handling).

Conventional bonding techniques using heat and pressure applied in a point-bonding process or by smooth calender rolls can be used, though such processes may cause undesired deformation of fibers or compaction of the web. A more preferred technique for bonding the microfibers is taught in U.S. Patent Application Publication No. US 2008/0038976 A1. Apparatus for performing this technique is illustrated in FIGS. 1, 5 and 6 of the drawings.

In brief summary, as applied to the present disclosure, this preferred technique involves subjecting the collected web of microfibers and sub-micrometer fibers to a controlled heating and quenching operation that includes a) forcefully passing through the web a gaseous stream heated to a temperature sufficient to soften the microfibers sufficiently to cause the microfibers to bond together at points of fiber intersection (e.g., at sufficient points of intersection to form a coherent or bonded matrix), the heated stream being applied for a discrete time too short to wholly melt the fibers, and b) immediately forcefully passing through the web a gaseous stream at a temperature at least 50° C. less than the heated stream to quench the fibers (as defined in the above-mentioned U.S. Patent Application Publication No. US 2008/0038976 A1, "forcefully" means that a force in addition to normal room pressure is applied to the gaseous stream to propel the stream through the web; "immediately" means as part of the same operation, i.e., without an intervening time of storage as occurs when a web is wound into a roll before the next processing step). As a shorthand term this technique is described as the quenched flow heating technique, and the apparatus as a quenched flow heater.

It has been found that the sub-micrometer fibers do not substantially melt or lose their fiber structure during the bonding operation, but remain as discrete microfibers with their original fiber dimensions. Without wishing to be bound by any particular theory, Applicant's believe that sub-micrometer fibers have a different, less crystalline morphology than microfibers, and we theorize that the limited heat applied to the web during the bonding operation is exhausted in developing crystalline growth within the sub-micrometer fibers before melting of the sub-micrometer fibers occurs. Whether this theory is correct or not, bonding of the microfibers without substantial melting or distortion of the sub-micrometer fibers does occur and may be beneficial to the properties of the finished web.

A variation of the described method, taught in more detail in the aforementioned U.S. Patent Application Publication No. US 2008/0038976 A1, takes advantage of the presence of two different kinds of molecular phases within microfibers—one kind called crystallite-characterized molecular phases because of a relatively large presence of chain-extended, or strain-induced, crystalline domains, and a second kind called amorphous-characterized phases because of a relatively large presence of domains of lower crystalline order (i.e., not chain-extended) and domains that are amorphous, though the latter may have some order or orientation of a degree insufficient for crystallinity. These two different kinds of phases, which need not have sharp boundaries and can exist in mixture with one another, have different kinds of properties, including different melting and/or softening characteristics: the first phase characterized by a larger presence of chain-extended crystalline domains melts at a temperature (e.g., the melting point of the chain-extended crystalline domain) that is higher than the temperature at which the second phase melts or softens (e.g., the glass transition temperature of the amorphous domain as modified by the melting points of the lower-order crystalline domains).

In the stated variation of the described method, heating is at a temperature and for a time sufficient for the amorphous-characterized phase of the fibers to melt or soften while the crystallite-characterized phase remains unmelted. Generally, the heated gaseous stream is at a temperature greater than the onset melting temperature of the polymeric material of the fibers. Following heating, the web is rapidly quenched as discussed above.

Treatment of the collected web at such a temperature is found to cause the microfibers to become morphologically refined, which is understood as follows (we do not wish to be bound by statements herein of our "understanding," which generally involve some theoretical considerations). As to the amorphous-characterized phase, the amount of molecular material of the phase susceptible to undesirable (softening-impeding) crystal growth is not as great as it was before treatment. The amorphous-characterized phase is understood to have experienced a kind of cleansing or reduction of molecular structure that would lead to undesirable increases in crystallinity in conventional untreated fibers during a thermal bonding operation. Treated fibers of certain exemplary embodiments of the present invention may be capable of a kind of "repeatable softening," meaning that the fibers, and particularly the amorphous-characterized phase of the fibers, will undergo to some degree a repeated cycle of softening and resolidifying as the fibers are exposed to a cycle of raised and lowered temperature within a temperature region lower than that which would cause melting of the whole fiber.

In practical terms, repeatable softening is indicated when a treated web (which already generally exhibits a useful bonding as a result of the heating and quenching treatment) can be heated to cause further autogenous bonding of the fibers. The cycling of softening and resolidifying may not continue indefinitely, but it is generally sufficient that the fibers may be initially bonded by exposure to heat, e.g., during a heat treatment according to certain exemplary embodiments of the present invention, and later heated again to cause re-softening and further bonding, or, if desired, other operations, such as calendering or re-shaping. For example, a web may be calendered to a smooth surface or given a nonplanar shape, e.g., molded into a face mask, taking advantage of the improved bonding capability of the fibers (though in such cases the bonding is not limited to autogenous bonding).

While the amorphous-characterized, or bonding, phase has the described softening role during web-bonding, calendering, shaping or other like operation, the crystallite-characterized phase of the fiber also may have an important role, namely to reinforce the basic fiber structure of the fibers. The crystallite-characterized phase generally can remain unmelted during a bonding or like operation because its melting point is higher than the melting/softening point of the amorphous-characterized phase, and it thus remains as an intact matrix that extends throughout the fiber and supports the fiber structure and fiber dimensions.

Thus, although heating the web in an autogenous bonding operation may cause fibers to weld together by undergoing some flow and coalescence at points of fiber intersection, the basic discrete fiber structure is substantially retained over the length of the fibers between intersections and bonds; preferably, the cross-section of the fibers remains unchanged over the length of the fibers between intersections or bonds formed during the operation. Similarly, although calendering of a web may cause fibers to be reconfigured by the pressure and heat of the calendering operation (thereby causing the fibers to permanently retain the shape pressed upon them during calendering and make the web more uniform in thickness), the fibers generally remain as discrete fibers with a consequent retention of desired web porosity, filtration, and insulating properties.

As shown in FIGS. 6 and 7, in a preferred method of carrying out certain exemplary embodiments of the present disclosure, a formed composite nonwoven fibrous web, for example, composite nonwoven fibrous web 302 of FIG. 1a, is carried by the moving collector 19 (see FIG. 2) under a controlled-heating device 200 mounted above the collector 19. The exemplary heating device 200 comprises a housing 201 which is divided into an upper plenum 202 and a lower plenum 203. The upper and lower plenums are separated by a plate 204 perforated with a series of holes 205 that are typically uniform in size and spacing. A gas, typically air, is fed into the upper plenum 202 through openings 206 from conduits 207, and the plate 204 functions as a flow-distribution means to cause air fed into the upper plenum to be rather uniformly distributed when passed through the plate into the lower plenum 203. Other useful flow-distribution means include fins, baffles, manifolds, air dams, screens or sintered plates, i.e., devices that even the distribution of air.

In the illustrative heating device 200 the bottom wall 208 of the lower plenum 203 is formed with an elongated slot 209 through which an elongated or knife-like stream 210 of heated air from the lower plenum is blown onto the composite nonwoven fibrous web 302 traveling on the collector 19 below the heating device 200 (the composite nonwoven fibrous web 302 and collector 19 are shown partly broken away in FIG. 7). The air-exhaust device 14 preferably extends sufficiently to lie under the slot 209 of the heating device 200 (as well as extending downweb a distance 218 beyond the heated stream 210 and through an area marked 220, as will be discussed below). Heated air in the plenum is thus under an internal pressure within the plenum 203, and at the slot 209 it is further under the exhaust vacuum of the air-exhaust device 14. To further control the exhaust force a perforated plate 211 may be positioned under the collector 19 to impose a kind of back pressure or flow-restriction means that assures the stream 210 of heated air will spread to a desired extent over the width or heated area of the collected composite nonwoven fibrous web 302 and be inhibited in streaming through possible lower-density portions of the collected mass. Other useful flow-restriction means include screens or sintered plates.

The number, size and density of openings in the plate 211 may be varied in different areas to achieve desired control. Large amounts of air pass through the microfiber-forming apparatus and must be disposed of as the fibers reach the collector in the region 215. Sufficient air passes through the web and collector in the region 216 to hold the web in place under the various streams of processing air. And sufficient openness is needed in the plate under the heat-treating region 217 to allow treating air to pass through the web, while sufficient resistance is provided to assure that the air is evenly distributed.

The temperature-time conditions should be controlled over the whole heated area of the mass. We have obtained best results when the temperature of the stream 210 of heated air passing through the web is within a range of 5° C., and preferably within 2 or even 1° C., across the width of the mass being treated (the temperature of the heated air is often measured for convenient control of the operation at the entry point for the heated air into the housing 201, but it also can be measured adjacent the collected web with thermocouples). In addition, the heating apparatus is operated to maintain a steady temperature in the stream over time, e.g., by rapidly cycling the heater on and off to avoid over- or under-heating. Preferably the temperature is held within one degree C. of the intended temperature when measured at one second intervals.

To further control heating, the mass is subjected to quenching quickly after the application of the stream 210 of heated air. Such a quenching can generally be obtained by drawing ambient air over and through the composite nonwoven fibrous web 302 immediately after the mass leaves the controlled hot air stream 210. Numeral 220 in FIG. 6 represents an area in which ambient air is drawn through the web by the air-exhaust device after the web has passed through the hot air stream. Actually, such air can be drawn under the base of the housing 201, e.g., in the area 220a marked on FIG. 6 of the drawings, so that it reaches the web almost immediately after the web leaves the hot air stream 210. And the air-exhaust device 14 extends along the collector for a distance 218 beyond the heating device 100 to assure thorough cooling and quenching of the whole composite nonwoven fibrous web 302. For shorthand purposes the combined heating and quenching apparatus is termed a quenched flow heater.

One aim of the quenching is to withdraw heat before undesired changes occur in the microfibers contained in the web. Another aim of the quenching is to rapidly remove heat from the web and the fibers and thereby limit the extent and nature of crystallization or molecular ordering that will subsequently occur in the fibers. By rapid quenching from the molten/softened state to a solidified state, the amorphous-characterized phase is understood to be frozen into a more purified crystalline form, with reduced molecular material that can interfere with softening, or repeatable softening, of the fibers. For some purposes, quenching may not be absolutely required though it is strongly preferred for most purposes.

To achieve quenching the mass is desirably cooled by a gas at a temperature at least 50° C. less than the nominal melting point; also the quenching gas is desirably applied for a time on the order of at least one second (the nominal melting point is often stated by a polymer supplier; it can also be identified with differential scanning calorimetry, and for purposes herein, the "Nominal Melting Point" for a polymer is defined as the peak maximum of a second-heat, total-heat-flow DSC plot in the melting region of a polymer if there is only one maximum in that region; and, if there are more than one maximum indicating more than one melting point (e.g., because of the presence of two distinct crystalline phases), as the temperature at which the highest-amplitude melting peak occurs). In any event the quenching gas or other fluid has sufficient heat capacity to rapidly solidify the fibers.

An advantage of certain exemplary embodiments of the present invention may be that the sub-micrometer fibers held within a microfiber web may be better protected against compaction than they would be if present in an all-sub-micrometer fiber layer. The microfibers are generally larger, stiffer and stronger than the sub-micrometer fibers, and they can be made from material different from that of the microfibers. The presence of the microfibers between the sub-micrometer fibers and an object applying pressure may limit the application of crushing force on the sub-micrometer fibers. Especially in the case of sub-micrometer fibers, which can be quite fragile, the increased resistance against compaction or crushing that may be provided by certain exemplary embodiments of the present invention offers an important benefit. Even when webs according to the present disclosure are subjected to pressure, e.g., by being rolled up in jumbo storage rolls or in secondary processing, webs of the present disclosure may offer good resistance to compaction of the web, which could otherwise lead to increased pressure drop and poor loading performance for filters. The presence of the microfibers also may add other properties such as web strength, stiffness and handling properties.

The diameters of the fibers can be tailored to provide needed filtration, acoustic absorption, and other properties. For example it may be desirable for the microfibers to have a median diameter of 5 to 50 micrometers (μm) and the sub-micrometer fibers to have a median diameter from 0.1 μm to less than 1 μm, for example, 0.9 μm. Preferably the microfibers have a median diameter between 5 μm and 50 μm, whereas the sub-micrometer fibers preferably have a median diameter of 0.5 μm to less than 1 μm, for example, 0.9 μm.

As previously stated, certain exemplary embodiments of the present invention may be particularly useful to combine very small microfibers, for example ultrafine microfibers having a median diameter of from 1 μm to about 2 μm, with the sub-micrometer fibers. Also, as discussed above, it may be desirable to form a gradient through the web, e.g., in the relative proportion of sub-micrometer fibers to microfibers over the thickness of the web, which may be achieved by varying process conditions such as the air velocity or mass rate of the sub-micrometer fiber stream or the geometry of the intersection of the microfiber and sub-micrometer fiber streams, including the distance of the die from the microfiber stream and the angle of the sub-micrometer fiber stream. A higher concentration of sub-micrometer fibers near one edge of a composite nonwoven fibrous web according to the present disclosure may be particularly advantageous for gas and/or liquid filtration applications.

In preparing microfibers or sub-micrometer fibers according to various embodiments of the present disclosure, different fiber-forming materials may be extruded through different orifices of a meltspinning extrusion head or meltblowing die so as to prepare webs that comprise a mixture of fibers. Various procedures are also available for electrically charging a nonwoven fibrous web to enhance its filtration capacity: see e.g., U.S. Pat. No. 5,496,507 (Angadjivand).

If a web could be prepared from the sub-micrometer fibers themselves, such a web would be flimsy and weak. However, by incorporating the population of sub-micrometer fibers with a population of microfibers in a coherent, bonded, oriented composite fibrous structure, a strong and self-supporting web or sheet material can be obtained, either with or without an optional support layer.

In addition to the foregoing methods of making a composite nonwoven fibrous web, one or more of the following process steps may be carried out on the web once formed:

(1) advancing the composite nonwoven fibrous web along a process pathway toward further processing operations;

(2) bringing one or more additional layers into contact with an outer surface of the sub-micrometer fiber component, the microfiber component, and/or the optional support layer;

(3) calendering the composite nonwoven fibrous web;

(4) coating the composite nonwoven fibrous web with a surface treatment or other composition (e.g., a fire retardant composition, an adhesive composition, or a print layer);

(5) attaching the composite nonwoven fibrous web to a cardboard or plastic tube;

(6) winding-up the composite nonwoven fibrous web in the form of a roll;

(7) slitting the composite nonwoven fibrous web to form two or more slit rolls and/or a plurality of slit sheets;

(8) placing the composite nonwoven fibrous web in a mold and molding the composite nonwoven fibrous web into a new shape;

(9) applying a release liner over an exposed optional pressure-sensitive adhesive layer, when present; and

(10) attaching the composite nonwoven fibrous web to another substrate via an adhesive or any other attachment device including, but not limited to, clips, brackets, bolts/screws, nails, and straps.

D. Methods of Using Composite Nonwoven Fibrous Webs

The present disclosure is also directed to methods of using the composite nonwoven fibrous webs of the present disclosure in a variety of absorption applications. In a further aspect, the disclosure relates to an article comprising a composite nonwoven fibrous web including a population of sub-micrometer fibers having a median diameter less than one micrometer (μm), and a population of microfibers having a median diameter of at least 1 μm, wherein at least, one of the fiber populations is oriented, and the composite nonwoven fibrous web has a thickness and exhibits a Solidity of less than 10%. In exemplary embodiments, the article may be used as a gas filtration article, a liquid filtration article, a sound absorption article, a surface cleaning article, a cellular growth support article, a drug delivery article, a personal hygiene article, or a wound dressing article.

For example, a low Solidity sub-micrometer composite nonwoven fibrous web of the present disclosure may be advantageous in gas filtration applications due to the reduced pressure drop that results from lower Solidity. Decreasing the Solidity of a sub-micrometer fiber web will generally reduce its pressure drop. Lower pressure drop increase upon particulate loading of low Solidity sub-micrometer composite nonwoven fibrous web of the present disclosure may also result. Current technology for forming particle-loaded sub-micrometer fibers results in much higher pressure drop than for coarser microfiber webs, partially due to the higher Solidity of the fine sub-micrometer fiber web.

In addition, the use of sub-micrometer fibers in gas filtration may be particularly advantageous due to the improved particle capture efficiency that sub-micrometer fibers may provide. In particular, sub-micrometer fibers may capture small diameter airborne particulates better than coarser fibers. For example, sub-micrometer fibers may more efficiently capture airborne particulates having a dimension smaller than about 1000 nanometers (nm), more preferably smaller than about 500 nm, even more preferably smaller than about 100 nm, and most preferably below about 50 nm. Gas filters such as this may be particularly useful in personal protection respirators; heating, ventilation and air conditioning (HVAC) filters; automotive air filters (e.g. automotive engine air cleaners, automotive exhaust gas filtration, automotive passenger compartment air filtration); and other gas-particulate filtration applications.

Liquid filters containing sub-micrometer fibers with low Solidity in the form of composite nonwoven fibrous webs of the present disclosure may also have the advantage of improved depth loading while maintaining small pore size for capture of sub-micrometer, liquid-borne particulates. These properties improve the loading performance of the filter by allowing the filter to capture more of the challenge particulates without plugging.

A low Solidity sub-micrometer fiber-containing composite nonwoven fibrous web of the present disclosure may also be a preferred substrate for supporting a membrane. The low Solidity fine web could act a both a physical support for the membrane, but also as a depth pre-filter, enhancing the life of the membrane. The use of such a system could act as a highly effective symmetric or asymmetric membrane. Applications for such membranes include ion-rejection, ultrafiltration, reverse osmosis, selective binding and/or adsorption, and fuel cell transport and reaction systems.

Low Solidity sub-micrometer composite nonwoven fibrous webs of the present disclosure may also be useful synthetic matrices for promoting cellular growth. The open structure with fine sub-micrometer fibers may mimic naturally occurring systems and promotes more in vivo-like behavior. This is in contrast to current products (such as Donaldson ULTRA-WEB™ Synthetic ECM, available from Donaldson Corp., Minneapolis, Minn.) where high Solidity fiber webs act as a synthetic support membrane, with little or no penetration of cells within the fiber matrix.

The structure provided by the composite nonwoven fibrous webs of the present disclosure may also be an effective wipe for surface cleaning, where the fine sub-micrometer fibers form a soft wipe, while low Solidity has the advantage of providing a reservoir for cleaning agents and high pore volume for trapping debris.

In one particular exemplary embodiment, the method of using a composite nonwoven fibrous article comprises a method of absorbing sound in an area, wherein the method comprises the steps of surrounding at least a portion of the area with a sub-micrometer fiber component, wherein the sub-micrometer fiber component comprising fibers having a median fiber diameter of less than 1 μm.

For acoustic and thermal insulation applications, providing the fine sub-micrometer fibers in a low Solidity form improves acoustic absorbance by exposing more of the surface area of the sub-micrometer fibers, as well as specifically improving low frequency acoustic absorbance by allowing for a thicker web for a given basis weight. In thermal insulation applications in particular, a low Solidity fine sub-micrometer fiber insulation containing sub-micrometer fibers would have a soft feel and high drapability, while providing a very low Solidity web for trapping insulating air. In some embodiments of an acoustic and/or thermal insulation article, an entire area may be surrounded by a composite nonwoven fibrous web including a sub-micrometer fiber component, provided alone or on a support layer. The support structure and the fine sub-micrometer fiber population(s) need not be homogeneously dispersed within one another. There may be advantages in cushioning, resiliency and filter loading for asymmetric loading to provide ranges of pore sizes, higher density regions, exterior skins or flow channels.

EXAMPLES

Exemplary embodiments of the present invention have been described above and are further illustrated below by way of the following Examples, which are not to be construed in any way as imposing limitations upon the scope of the present invention. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims. Furthermore, notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Fabrication of Composite Nonwoven Fibrous Webs

Exemplary composite nonwoven fibrous webs were formed by in-process mixing the fibers resulting from a spunbond process with sub-micrometer fibers produced from the process described in U.S. Pat. No. 4,536,361. The spunbond process used was an open system known to produce oriented fibers, as described by U.S. Pat. No. 6,824,372. The process was configured such that the fibers from the sub-micrometer fiber die were blown into the spunbond fiber curtain below the air attenuator but above the collector belt.

The sub-micrometer fiber production process used grade 3960 polypropylene from Total Petrochemicals, Houston, Tex. The polymer was melted using a ¾" diameter single screw extruder and fed to the sub-micrometer fiber forming die. The die was heated to 290° C., and was fed with polymer at a rate of 7 grams per minute. Room temperature air was fed to the die at a pressure of 80 pounds per square inch. The spunbond fiber production process also used grade 3960 polypropylene and had a process temperature of 230° C. The polymer flow rate was 0.2 grams per hole per minute. The fiber attenuator was set at 4.4 standard cubic meters of air per minute.

Two fiber samples were collected. The first sample, Sample 1, was bonded after fiber mixing by passing the web through a through air bonder set at 150° C. before winding. The second sample, Sample 2, was rolled up directly after mixing without the additional bonding step.

The two samples were measured for median fiber diameter, basis weight, thickness (one mil equals 25 micrometers), and Solidity. To measure median fiber diameter, a sample from each web was sputter coated with gold-palladium and examined in a scanning electron microscope. The median diameters of the two populations of fibers in the micrographs were measured, and the median diameters reported. For each sample at least 50 individual fibers of each population were measured. Due to the large diameter differences between the spunbond fibers, which were predominantly microfibers, and the sub-micrometer fibers, the mean diameters of both fiber populations generally corresponds to a value close to but slightly below the spunbond fiber diameter. The results of the measurements are presented in Table I.

TABLE I

| Sample | Sub-Micrometer Fiber Median Diameter (micrometers) | Spunbond Fiber Median Diameter (micrometers) | Basis Weight (gsm) | Thickness (mils) | Solidity (%) |
|---|---|---|---|---|---|
| Sample 1 | 0.86 | 11.23 | 165 | 72 | 9.91 |
| Sample 2 | 0.48 | 10.36 | 146 | 131 | 4.83 |

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the present invention. Thus, the appearances of the phrases such as "in one or more embodiments," "in certain embodiments," "in one embodiment" or "in an embodiment" in various places throughout this specification are not necessarily referring to the same embodiment of the present invention. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g. 1 to 5 includes 1, 1.5, 2, 2.75, 3, 3.80, 4, and 5). In addition, all numbers used herein are assumed to be modified by the term 'about'. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

The invention claimed is:

1. A composite nonwoven fibrous web comprising:
   a population of sub-micrometer fibers having a median diameter less than one micrometer (μm); and
   a population of meltblown microfibers having a median diameter of at least 1 μm, wherein at least one of the fiber populations is oriented, and further wherein the composite nonwoven fibrous web is formed as a single layer having a thickness and exhibiting a Solidity of less than 10%,
   wherein the population of sub-micrometer fibers is intermixed with the population of microfibers to form an inhomogeneous mixture of fibers wherein a ratio of the number of sub-micrometer fibers to the number of microfibers varies from a peak value proximate a centerline defined by the half-thickness of the composite nonwoven fibrous web, to a lower value at a major surface of the composite nonwoven fibrous web.

2. The web of claim 1, wherein the population of sub-micrometer fibers has a median fiber diameter ranging from about 0.2 μm to about 0.9 μm, optionally wherein the population of microfibers has a median fiber diameter ranging from about 2 μm to about 50 μm.

3. The web of claim 1, wherein at least one of the population of sub-micrometer fibers and the population of microfibers comprises polymeric fibers, optionally wherein the polymeric fibers comprise polypropylene, polyethylene, polyester, polyethylene terephthalate, polybutylene terephthalate, polyamide, polyurethane, polybutene, polylactic acid, polyvinyl alcohol, polyphenylene sulfide, polysulfone, liquid crystalline polymer, polyethylene-co-vinylacetate, polyacrylonitrile, cyclic polyolefin, polyoxymethylene, polyolefinic thermoplastic elastomers, or a combination thereof.

4. The web of claim 1, wherein the population of sub-micrometer fibers overlays the population of microfibers.

5. The web of claim 1, further comprising a support layer, optionally wherein the support layer comprises a nonwoven fabric, a woven fabric, a knitted fabric, a foam layer, a film, a paper layer, an adhesive-backed layer, or a combination thereof.

6. The web of claim 5, wherein the support layer comprises a web of bonded staple fibers, further wherein the support layer is bonded using thermal bonding, adhesive bonding, powdered binder, hydroentangling, needlepunching, calendering, or a combination thereof.

7. The web of claim 5, further comprising an adhesive layer formed on the support layer opposite the overlayer.

8. A method of making a composite nonwoven fibrous web, comprising:
   a. forming a population of sub-micrometer fibers having a median fiber diameter of less than one micrometer (μm);
   b. forming a population of meltblown microfibers having a median fiber diameter of at least 1 μm; and
   c. combining the sub-micrometer fibers and microfibers into a single layer composite nonwoven fibrous web, wherein at least one of the fiber populations is oriented, and further wherein the single layer composite nonwoven fibrous web has a thickness and exhibits a Solidity of less than 10%,
      wherein the population of sub-micrometer fibers is intermixed with the population of microfibers to form an inhomogeneous mixture of fibers wherein a ratio of the number of sub-micrometer fibers to the number of microfibers varies from a peak value proximate a centerline defined by the half-thickness of the composite nonwoven fibrous web, to a lower value at a major surface of the composite nonwoven fibrous web.

9. The method of claim 8, wherein forming a population of sub-micrometer fibers having a median fiber diameter of less than 1 μm comprises melt blowing, melt spinning, electrospinning, gas jet fibrillation, or a combination thereof.

10. The method of claim 8, wherein the population of microfibers has a median fiber diameter from 5 to 50 μm.

11. The method of claim 8, wherein combining the sub-micrometer and microfibers into a composite nonwoven fibrous web comprises mixing fiber streams, hydroentangling, wet forming, plexifilament formation, or a combination thereof.

12. An article comprising the composite nonwoven fibrous web prepared according to the method of claim 8, selected from the group consisting of a gas filtration article, a liquid filtration article, a sound absorption article, a surface cleaning article, a cellular growth support article, a drug delivery article, a personal hygiene article, and a wound dressing article.

* * * * *

UNITED STATES PATENT AND TRADEMARK OFFICE
CERTIFICATE OF CORRECTION

| | | |
|---|---|---|
| PATENT NO. | : 8,906,815 B2 | Page 1 of 1 |
| APPLICATION NO. | : 12/810113 | |
| DATED | : December 9, 2014 | |
| INVENTOR(S) | : Eric Moore | |

It is certified that error appears in the above-identified patent and that said Letters Patent is hereby corrected as shown below:

In the Specification

Column 10, Line 3
Delete "thereof" and insert -- thereof. --, therefor.

Column 27, Line 38
Delete "a" and insert -- as --, therefor.

Signed and Sealed this
Thirtieth Day of June, 2015

Michelle K. Lee
*Director of the United States Patent and Trademark Office*